US011059849B2

(12) United States Patent
Ybert et al.

(10) Patent No.: US 11,059,849 B2
(45) Date of Patent: Jul. 13, 2021

(54) MODIFIED NUCLEOTIDES FOR SYNTHESIS OF NUCLEIC ACIDS, A KIT CONTAINING SUCH NUCLEOTIDES AND THEIR USE FOR THE PRODUCTION OF SYNTHETIC NUCLEIC ACID SEQUENCES OR GENES

(71) Applicant: DNA Script, Le Kremlin-Bicêtr (FR)

(72) Inventors: Thomas Ybert, Paris (FR); Sylvain Gariel, Paris (FR)

(73) Assignee: DNA Script, Le Kremlin-Bicêtre (FR)

( * ) Notice: Subject to any disclaimer, the term of this patent is extended or adjusted under 35 U.S.C. 154(b) by 684 days.

(21) Appl. No.: 15/507,853

(22) PCT Filed: Sep. 1, 2015

(86) PCT No.: PCT/FR2015/052310
§ 371 (c)(1),
(2) Date: Mar. 1, 2017

(87) PCT Pub. No.: WO2016/034807
PCT Pub. Date: Mar. 10, 2016

(65) Prior Publication Data
US 2020/0231619 A1     Jul. 23, 2020

(30) Foreign Application Priority Data
Sep. 2, 2014  (FR) ..................................... 14 58194

(51) Int. Cl.
| C07H 21/04 | (2006.01) |
| C07H 19/10 | (2006.01) |
| C07H 19/20 | (2006.01) |
| C12P 19/34 | (2006.01) |

(52) U.S. Cl.
CPC ............. C07H 19/10 (2013.01); C07H 19/20 (2013.01); C12P 19/34 (2013.01)

(58) Field of Classification Search
CPC ..................................................... C07H 19/10
See application file for complete search history.

(56) References Cited

U.S. PATENT DOCUMENTS

| 4,772,691 A | 9/1988 | Herman |
| 5,047,524 A | 9/1991 | Andrus |
| 5,262,530 A | 11/1993 | Andrus |
| 5,436,143 A | 7/1995 | Hyman |
| 5,516,664 A | 5/1996 | Hyman |
| 5,602,000 A | 2/1997 | Hyman |
| 5,656,745 A | 8/1997 | Bischofberger |
| 5,744,595 A | 4/1998 | Srivastava |
| 5,763,594 A | 7/1998 | Hiatt |
| 5,798,210 A | 8/1998 | Canard |
| 5,808,045 A | 9/1998 | Hiatt |
| 5,872,244 A | 2/1999 | Hiatt |
| 5,917,031 A | 6/1999 | Miura |
| 5,935,527 A | 8/1999 | Andrus |
| 5,990,300 A | 11/1999 | Hiatt et al. |
| 6,214,987 B1 | 4/2001 | Hiatt |
| 6,232,465 B1 | 5/2001 | Hiatt |
| 6,623,929 B1 | 9/2003 | Densham |
| 6,664,079 B2 | 12/2003 | Ju |
| 6,777,189 B2 | 8/2004 | Wei |
| 7,057,026 B2 | 1/2006 | Barnes |
| 7,078,499 B2 | 7/2006 | Odedra |
| 7,125,671 B2 | 10/2006 | Sood |
| 7,270,951 B1 | 9/2007 | Stemple |
| 7,345,159 B2 | 3/2008 | Ju |
| 7,407,757 B2 | 8/2008 | Brenner |
| 7,544,794 B1 | 6/2009 | Benner |
| 7,566,537 B2 | 7/2009 | Balasubramanian |
| 7,635,578 B2 | 12/2009 | Ju |
| 7,713,698 B2 | 5/2010 | Ju |
| 7,790,869 B2 | 9/2010 | Balasubramanian |
| 7,932,025 B2 | 4/2011 | Carr |
| 7,939,259 B2 | 5/2011 | Kokoris |
| 8,034,923 B1 | 10/2011 | Benner |
| 8,212,020 B2 | 7/2012 | Benner |
| 8,263,335 B2 | 9/2012 | Carr |
| 8,394,586 B2 | 3/2013 | Balasubramanian |

(Continued)

FOREIGN PATENT DOCUMENTS

| EP | 1655381 | 5/2006 |
| EP | 1165786 B1 | 7/2008 |

(Continued)

OTHER PUBLICATIONS

Becker et al, "The enzymatic cleavage of phosphate termini from polynucleotides," J. Biol. Chem., 242(5): 936-950 (1967).
Cameron et al, "3'-phosphatase activity in T4 polynucleotide kinase," Biochemistry, 16(23): 5120-5126 (1977).
Canard et al, "Catalytic editing properties of DNA polymerases," Proc. Natl. Acad. Sci., 92: 10859-10863 (1995).
Canard et al, "DNA polymerase fluorescent substrates with reversible 3'-tags," Gene, 148: 1-6 (1994).
Chen et al, "The history and advances of reversible terminators used in new generations of sequencing technology," Genomics Proteomics Bioinformatics, 11: 34-40 (2013).

(Continued)

*Primary Examiner* — Kimberly Chong
(74) *Attorney, Agent, or Firm* — Edward J. Baba; Kathleen Y. Rao; Bozicevic, Field & Francis LLP

(57) ABSTRACT

A modified nucleotide, intended for the synthesis of long chain nucleic acids by enzymatic processes, comprising a "natural" nitrogenous base or a natural nitrogenous base analogue, a ribose or deoxyribose carbohydrate, and at least one phosphate group, characterized in that said nucleotide comprises at least one R group, termed the modifier group, carried by said nitrogenous base or analogue and/or by the oxygen in position 3' of the ribose or deoxyribose molecule, making it possible to block the polymerization of said nucleotide and/or to allow the interaction of said nucleotide with another molecule, such as a protein, during the nucleic acid synthesis, R comprising at least one functional terminal group.

12 Claims, 13 Drawing Sheets

Specification includes a Sequence Listing.

(56) References Cited

U.S. PATENT DOCUMENTS

| | | |
|---|---|---|
| 8,674,086 B2 | 3/2014 | Liu |
| 8,808,988 B2 | 8/2014 | Zhao |
| 8,808,989 B1 | 8/2014 | Efcavitch |
| 9,121,062 B2 | 9/2015 | Balasubramanian |
| 9,388,463 B2 | 7/2016 | Balasubramanian |
| 9,896,709 B2 | 2/2018 | Makarov |
| 2008/0161548 A1 | 7/2008 | Gupta |
| 2012/0136143 A1 | 5/2012 | Getts |
| 2013/0005612 A1 | 1/2013 | Carr |
| 2014/0363851 A1 | 12/2014 | Efcavitch |
| 2014/0363852 A1 | 12/2014 | Efcavitch |

FOREIGN PATENT DOCUMENTS

| | | |
|---|---|---|
| WO | 1991/06678 | 5/1991 |
| WO | 1996/07669 | 5/1996 |
| WO | WO2004/018497 | 3/2004 |
| WO | 2004048397 | 6/2004 |
| WO | 2005/059096 | 6/2005 |
| WO | 2016/034807 | 3/2016 |

OTHER PUBLICATIONS

Ferrero et al, "Chemoenzymatic transformations in nucleoside chemistry," Monatshefte fur Chemie, 131: 585-616 (2000).

Guo et al, "An integrated system for DNA sequencing by synthesis using novel nucleotide analogues," Acc. Chem. Res., 43(4): 551-563 (2010).

Ju et al, "Four-color DNA sequencing by synthesis using cleavable fluorescent nucleotide reversible terminators," Proc. Natl. Acad. Sci., 103(52): 19635-19640 (2006).

Knapp et al, "Fluoride-Cleavable, Fluorescently Labelled Reversible Terminators: Synthesis and Use in Primer Extension," Chem. Eur. J., 17: 2903-2915 (2011).

Kobayashi et al, "A microfluidic device for conducting gas-liquid-solid hydrogenation reactions," Science, 304: 1305-1308 (2004).

Li et al, "A photocleavable fluorescent nucleotide for DNA sequencing and analysis," Proc. Natl. Acad. Sci., 100(2): 414-419 (2003).

Lin et al, "Recent patents and advances in the next-generation sequencing technologies," Recent Patents in Biomedical Engineering, 2008(1): 60-67 (2008).

Motea et al, "Terminal deoxynucleotidyl transferase: The story of a misguided DNA polymerase," Biochim Biophys Acta, 1804(5): 1151-1166 (2010).

Olejnik et al, "Photocleavable biotin derivatives: A versatile approach for the isolation of biomolecules," Proc. Natl. Acad. Sci., 92: 7590-7594 (1995).

Palla et al, "DNA sequencing by synthesis using 3'-O-azidomethyl nucleotide reversible terminators and surface-enhanced Raman spectroscopic detection," RCS Adv. 4: 49342 (2014).

Rasolonjatovo et al, "Development of a new sequencing method: 3'-ester cleavage catalyzed by Taq DNA polymerase," Nucleosides & Nucleotides, 18(4&5): 1021-1022 (1999).

Schmitz et al, "Solid-phase enzymatic synthesis of oligonucleotides," Organic Lett., 1(11): 1729-1731 (1999).

Schott et al, "Single-step elongation of oligodeoxynucleotides using terminal deoxynucleotidyl transferase," Eur. J. Biochem., 143: 613-620 (1984).

Ud-Dean, "A theoretical model for template-free synthesis of long DNA sequence," Syst. Synth. Biol., 2: 67-73 (2008).

Uemura et al, "Regioselective deprotection of 3', 5'-O-acylated pyrimidine nucleosides by lipase and esterase," Tetrahedron Lett., 30(29): 3819-3820 (1989).

Written Opinion of the International Searching Authority for PCT/FR2015/051022 dated Sep. 2, 2016.

Wu et al, "3'-O-modified nucleotides as reversible terminators for pyrosequencing," Proc. Natl. Acad. Sci., 104(42): 16462-16467 (2007).

Guo et al, "Four-color DNA sequencing with 3'-O-modified nucleotide reversible terminators and chemically cleavable fluorescent dideoxynucleotides," Proc. Natl. Acad. Sci., 105(27): 9145-9150 (2008).

IPR2013-00128 re U.S. Pat. No. 7,057,026 Final Written Decision (Jul. 25, 2013).

IPR2013-00266 re U.S. Pat. No. 8,158,346 Final Written Decision (Oct. 28, 2014).

IPR2017-02172 re U.S. Pat. No. 7,566,537 Decision (Apr. 20, 2018).

Michelson et al, "Characterization of the homopolymer tailing reaction catalyzed by terminal deoxynucleotidyl transferase," J. Biol. Chem., 257(24): 14773-14782 (1982).

Wu, Thesis, "Molecular engineering of novel nucleotide analogues for DNA sequencing by synthesis," Columbia University, 2008.

Zavgorodny et al, "1-Alkylthioalkylation of nucleoside hydroxyl functions and its synthetic applications: A new versatile method in nucleoside chemistry," Tetrahedron Lett., 32(51): 7593-7596 (1991).

Guli Lat Gebeyehu et al: "Novel biotinylated nucleotide analogs for labeling and colorimetric detection of DNA" No. 15 ( 11). val. 15. No. 11. Jan. 1, 1987 (Jan. 1, 1987). pages.

Ani Lkumar R. Kore et al: 11 Synthesi s and Activity of Modified Cytidine 5'-Monophosphate Probes for T4 RNA Ligase 1 Nucleosides. Nucleotides & Nucleic Acids. vol. 28. No. 4. May 22, 2009 (May 22, 2009). pp. 292-302.

J.L. Flickinger et al: "Differential incorporation of biotinylated nucleotides by terminal deoxynucleotidyl transferase," Nucleic Acids Research. vo 1 • 20. No. 9. Jan. 1, 1992 (Jan. 1, 1992). pp. 2382-2382.

Petrie C R et al: "A Novel Biotinylated Adenylate Analogue Derived From Pyrazol003.4-D 3/4 Pyrimidine for Labeling DNA Probes" Bioconjugate Chemistry. ACS. Washington vo 1 • 2. No. 6. Nov. 1, 1991 (Nov. 1, 1991). pp. 441-446.

Beabealashvilli R S et al: "Nucleoside 5'-triphosphates modified at sugar residues as substrates for calf thymus terminal deoxynucleotidyl transferase and for AMV reverse transcriptase" Biochimica et Biophysica Acta . Gene Structure and Expression. Elsevier, Amsterdam. NL. val. 868. No. 2-3. Nov. 13, 1986 (Nov. 13, 1986). pp. 136-144.

De Swarup et al: "Synthesis of new biocarrier-nucleotide systems for cellular delivery in bacterial auxotrophic str". Tetrahedron, val. 70. No. 46. Jul. 30, 2014 (Jul. 30, 2014), pp. 8843-8851.

Search Report dated Oct. 30, 2015.

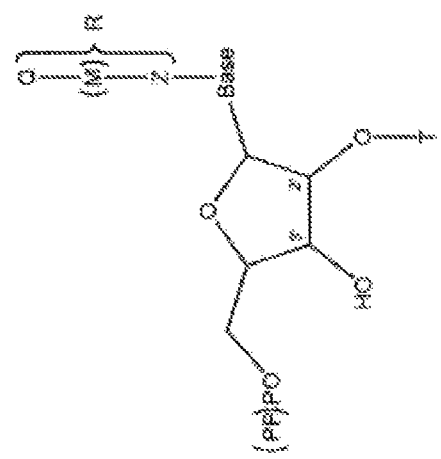
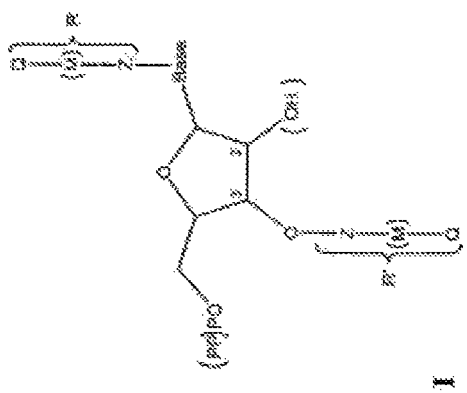
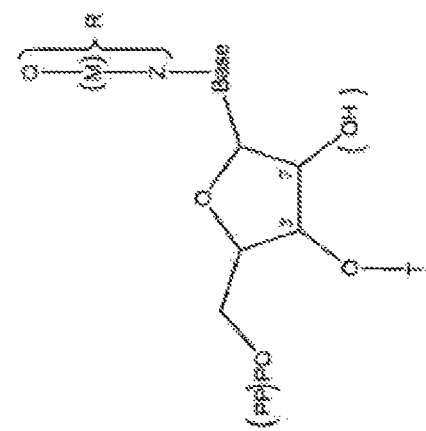
Fig. 1

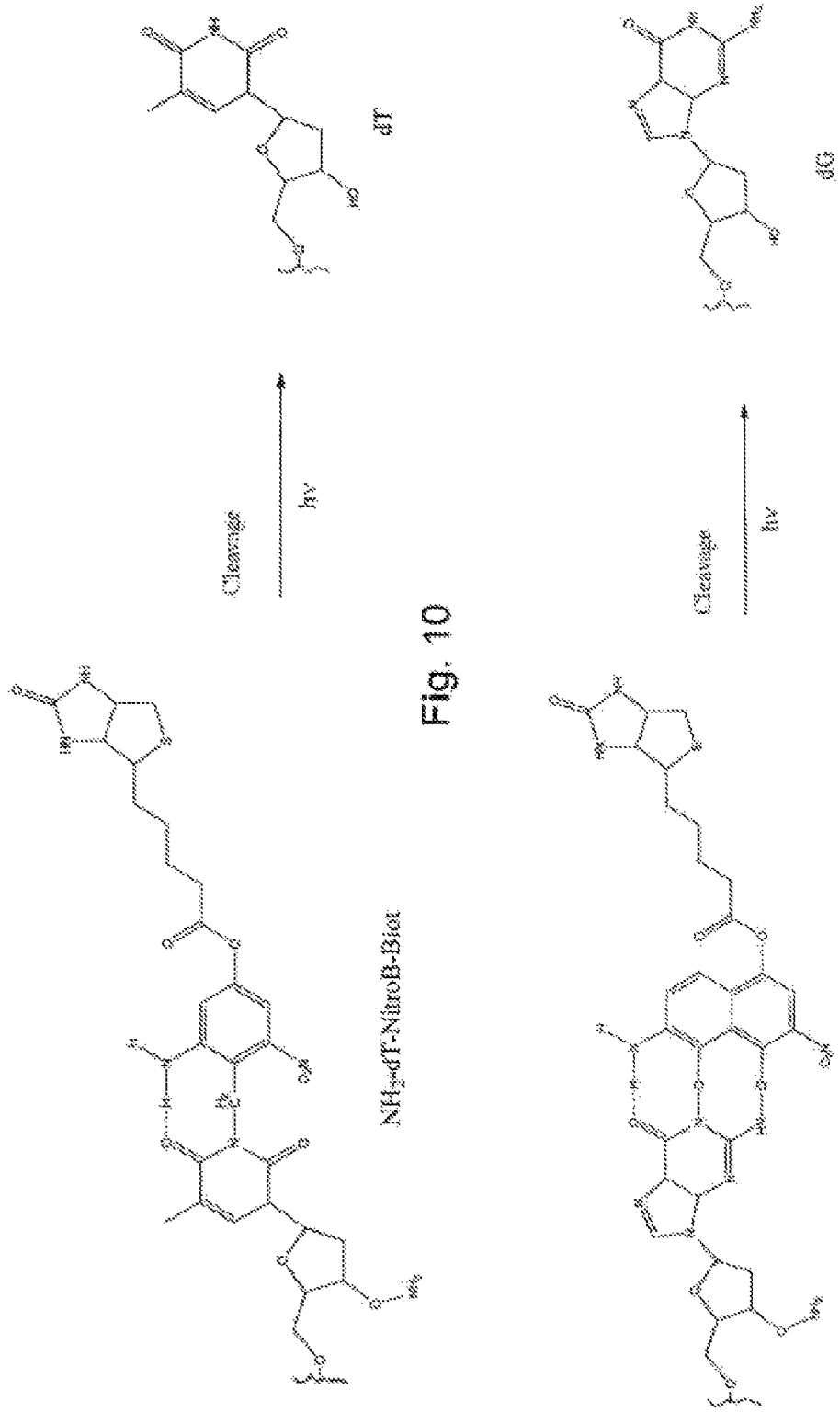

MODIFIED NUCLEOTIDES FOR SYNTHESIS OF NUCLEIC ACIDS, A KIT CONTAINING SUCH NUCLEOTIDES AND THEIR USE FOR THE PRODUCTION OF SYNTHETIC NUCLEIC ACID SEQUENCES OR GENES

RELATED APPLICATIONS

This application is a National Phase Application of PCT/FR2015/052310 filed on Sep. 1, 2015, which in turn claims the benefit of priority from French Patent No. 14 58194 filed on Sep. 2, 2014, the entirety of which are incorporated herein by reference.

BACKGROUND

Field of the Invention

The present invention falls within the field of the synthesis of functionalized copolymers of biological interest. It relates more particularly to nucleotides required for the synthesis of nucleic acids, in particular of very long nucleic acids, to a kit containing such nucleotides and to the use thereof for the production of synthetic nucleic acid sequences or genes.

PRIOR ART

To date, there are two major categories of in vitro nucleic acid synthesis: chemical syntheses and enzymatic syntheses.

The most common in vitro nucleic acid chemical synthesis method is the method of polymerization by means of phosphoramidites described by Adams et al. (1983, J. Amer. Chem. Soc. 105:661) and Froehler et al. (1983, Tetrahedron Lett. 24:3171). In this method, each nucleotide to be added is protected on the 5'-OH group so as to prevent uncontrolled polymerization of several nucleotides of the same type. Generally, the protection of the 5'-OH group is carried out with a trityl group. In order to prevent any degradation due to the use of powerful reagents, the bases borne by the nucleotides can also be protected. Generally, the protection used involves an isobutyryl group (Reddy et al. 1997, Nucleosides & Nucleotides 16:1589). After each incorporation of new nucleotides, the 5'-OH group of the last nucleotide of the chain undergoes a deprotection reaction for the purpose of making it available for the subsequent polymerization step. The nitrogenous bases borne by the nucleotides which make up the nucleic acid, themselves, are deprotected only after the complete polymerization has been finished.

These chemical synthesis methods proved to be expensive and dangerous to use owing to the nature of the reagents involved. Furthermore, they are inefficient for the synthesis of long nucleic acid fragments (fragments greater than about a hundred nucleotides).

With a view to developing methods of nucleic acid synthesis, in particular for the production of very long fragments with high yields, and also methods compatible with the already existing genetic elements, such as DNA plasmids, synthesis techniques have been developed which use enzymatic catalysts for carrying out the coupling reaction between the nucleotides, even in the absence of a template strand.

In some of these enzymatic synthesis methods, the enzyme enabling the polymerization is directly added to the natural nucleotides (Deng et al. 1983, Meth. Enzymol. 100:96). Starting from an initial nucleic acid fragment known as a primer, the polymerization enzyme and also nucleotides of one and the same type are added. The polymerization reaction is then initiated, and the nucleic acid grows sequentially by repetition of these steps of creating a phosphodiester bond, until said polymerization is stopped by a physical or chemical method.

The use of natural nucleotides (that is to say unmodified and unprotected nucleotides) leads to an uncontrolled polymerization resulting in a very heterogeneous mixture of nucleic acid molecules. This is because nothing prevents the addition of several nucleotides of one and the same type after a first addition. In practice, such a synthesis method proves to be unusable for the synthesis of nucleic acid fragments having a desired sequence.

The use of protected nucleotides makes it possible, to a certain extent, to solve this uncontrolled polymerization phenomenon. The protected nucleotides make it possible to stop the synthesis by totally or partially preventing the creation of phosphodiester bonds subsequent to that desired.

Nucleotides are the "monomers" used for nucleic acid synthesis. Their chemical properties and also their ability to react or not react guarantee that the desired synthesis takes place correctly. It is important to be able to polymerize the nucleotides one by one in the desired order in order to be able to synthesize a nucleic acid fragment comprising the desired sequence. This polymerization is equivalent to the addition of nucleotides one after another in an order which must be strictly adhered to. It is in particular necessary to take care that several nucleotides comprising the same nitrogenous base and introduced at the same time do not react in chain, leading to the uncontrolled growth of the oligomeric chain and, as a result, to the production of an erroneous nucleic acid sequence.

There are modified nucleotides comprising certain structural modifications compared with natural nucleotides, which give them certain advantages when they are used for nucleic acid synthesis. They are generally obtained by chemical or enzymatic modifications of the nucleotides naturally present in cells. Some modified nucleotides are said to be protected because they comprise chemical groups which prohibit the modification of a chemical function to be preserved during other reactions. The protective groups may be placed at various sites of the nucleotide molecule.

One particular class of protected nucleotides has a polymerization-reaction-terminating function. The role of these "chain-terminating" nucleotides consists in preventing excessive and undesired polymerization of the nucleotides introduced into the reaction medium. When a terminator nucleotide is incorporated into a nucleic acid molecule, it impedes the subsequent polymerization of another nucleotide. Thus, a single nucleotide can be added to each nucleic acid molecule during the elongation step. Even if the various nucleotides, making up the nucleic acid fragment to be synthesized, are introduced sequentially, it is necessary to use "terminator" nucleotides in order to prevent undesirable repetition phenomena.

The use of "terminator" nucleotides guarantees the reliability and reproducibility of nucleic acid synthesis methods, whether they are chemical or enzymatic. They can have a great influence on the synthesis performance levels of a given method.

The protected nucleotides used for the chemical synthesis of nucleic acids comprise, in the 5'-OH position, a protection by covalent bonding to a DMT (4,4'-dimethoxytrityl) group and, in the 3'-OH position, a phosphoramidite group acting as a catalyst for the polymerization reaction of the nucleotides with one another. These nucleotides comprising DMT and phosphoramidite groups are called protected phosphoramidite nucleotides. The protection against uncontrolled polymerization is provided by the DMT group protecting the 5'-OH. During chemical nucleic acid synthesis, a first deprotection phase, called detritylation, takes place in order to remove the DMT group and to obtain a 5'-OH group that is available to react with the nucleotide to be inserted. It is particularly important to have the most efficient deprotection reaction possible in order to allow the addition of the next nucleotide in all cases.

Protected phosphoramidite nucleotides are exclusively used during the chemical synthesis of nucleic acids. Their "terminator" function is in fact provided by the DMT group bonded to the 5'-OH. Since the chemical synthesis takes place in the 3' to 5' direction, the existence of a DMT group protecting the 5'-OH makes it possible to prevent any excessive polymerization until the next deprotection step.

Thus, protected phosphoramidite nucleotides are not suitable for enzymatic synthesis methods.

Some "terminator" nucleotides have also been developed for "second-generation" sequencing methods. However, in addition to being totally unsuitable for nucleic acid synthesis, the terminator nucleotides used for the sequencing have a certain number of totally unacceptable limitations.

The main limitation is their ability to be used by the elongation enzymes. This is because the fluorescent labels bonded to the terminator nucleotides for the sequencing have a considerable size. However, the elongation enzymes have an extremely small amount of space in their active site and thus have little chance of being able to accept, in order to polymerize them, terminator nucleotides housing imposing fluorescent groups, such as groups comprising conjugated aromatic rings.

Modern DNA sequencing techniques are based on complementary interactions between a template strand, the sequenced strand, and a strand undergoing elongation. Generally, the modified nucleotides used for the sequencing must have intact properties of pairing with their complementary nucleotides. The modified nucleotides should preserve these properties of interactions that are essential for their use. However, the nitrogenous bases which constitute the modified nucleotides for sequencing are analogs of natural nitrogenous bases such as adenine, guanine, thymine, uracil and cytosine, and thus do not have the same chemical structure: some atoms are substituted with others and some groups are added or deleted. These unnatural nitrogenous bases can have many drawbacks, such as that, for example, of not being recognized by living organisms.

Once incorporated, the terminator nucleotides are deprotected in order to allow the addition of the next nucleotide. The deprotection step involves a physical or chemical means which makes it possible to delete the group responsible for the terminator function. The other functional groups associated with the modified nucleotide are deleted during similar deprotection steps. Several deprotection steps are thus generally necessary during the various sequencing processes in order to be able to move to the determination of the next nucleotide. These various deprotection steps accumulate and multiply the use of powerful reagents or of extreme physical conditions which promote the degradation of the various species present in the reaction medium and in particular the degradation of the nucleic acids. Furthermore, a large number of deprotection steps considerably decreases the rapidity of the process and its performance levels.

Yet another major problem encountered during the use of modified nucleotides for sequencing is the appearance of scars after the deprotection steps. The various chemical structures which serve as a link between the functional groups and the nucleotide are capable of being broken during the deprotection steps. However, this breaking does not make it possible to separate all of the chemical bonding structures. Thus, more or less large parts of these structures remain attached to the nucleotides, despite the various deprotection steps. These residues have a very harmful effect on the sequencing process and on any use or modification of the nucleic acids in general.

Whatever the structure of the nucleotide retained, the existing modified nucleotides do not make it possible to meet the expectations of enzymatic synthesis methods. Their mediocre use by elongation enzymes, the positioning of the various functional groups, the systematic use of modified nitrogenous bases, the obligation of preserving the interactions with the complementary nucleotides, the numerous deprotection steps and the presence of residual scars prohibit the use of these nucleotides for enzymatic nucleic acid synthesis.

To date, there is therefore no satisfactory technical solution proposing protected nucleotides that are compatible with the enzymatic synthesis of nucleic acids, in particular for the enzymatic synthesis of very long nucleic acid fragments.

Aims of the Invention

A first aim of the invention is to provide modified nucleotides which are suitable for enzymatic nucleic acid synthesis.

Another aim of the invention is to provide natural nucleotides which are modified by various functional groups making it possible to render them compatible with their use during a nucleic acid synthesis process.

Another aim of the invention is to provide modified nucleotides which make it possible to synthesize very long nucleic acids, that is to say nucleic acids of at least several hundred or several thousand nucleotides, and more particularly according to the process described in the patent application by the same applicant, not yet published, FR 14-53455.

DESCRIPTION OF THE INVENTION

To this effect, the present invention provides a modified nucleotide, intended for the enzymatic synthesis of nucleic acids, such as long-chain nucleic acids, comprising a "natural" nitrogenous base or a natural nitrogenous base analog, a ribose or deoxyribose carbohydrate, and at least one phosphate group, characterized in that it comprises at least one R or R' group, called modifier group, borne:
  by said natural nitrogenous base or analog,
  and/or by the oxygen in position 3' of the ribose or deoxyribose molecule, making it possible to block the polymerization of said nucleotide (the modifier group is then a protective group) and/or to enable the interaction of said nucleotide with another molecule, different than another nucleotide, such as a protein, during nucleic acid synthesis, R comprising at least one functional end group (which may also be called effector group).

More particularly, the modifier group is advantageously not a large group, such as a group comprising conjugated aromatic rings, in particular so as to allow access of the enzyme to the reaction site.

The nucleotide according to the invention may be a monophosphate, a diphosphate or a triphosphate, the phosphate group(s) being free, that is to say unmodified.

The nucleotide according to the invention is in the form of one of formulae (I), (III) and (IV) below:

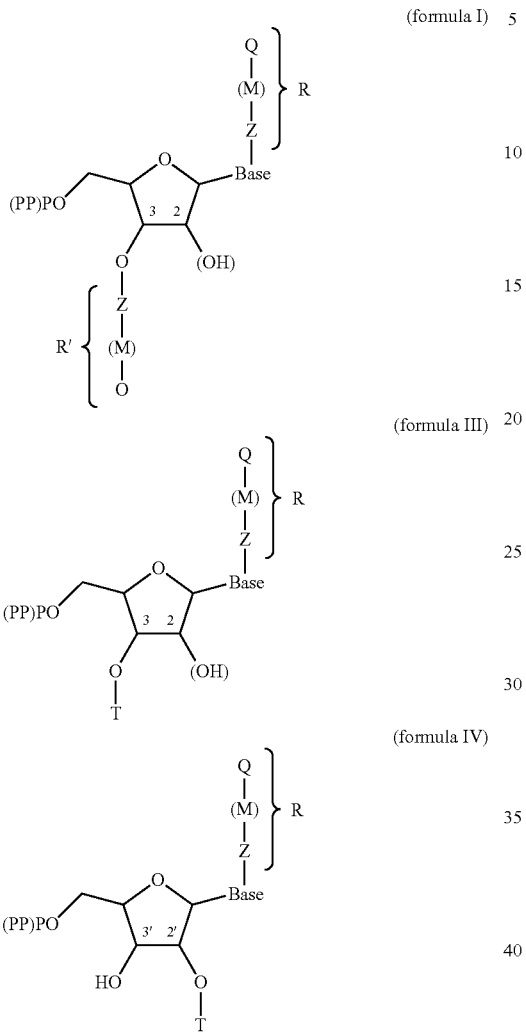

(formula I)

(formula III)

(formula IV)

in which:
(PP)PO represents a mono-, di- or triphosphate group,
(OH) describes the possibility of a ribose or deoxyribose molecule,
T is a hydrogen, or a cleavable radical chosen from —NH$_2$, —N$_3$, —(C=O)H, —C$_n$H$_{2n+1}$ with n between 1 and 30, preferably between 1 and 12, -trimethylsilyl, -phosphate, —SO$_3$, —(C=O)OC$_n$H$_{2n+1}$ with n between 1 and 30, preferably between 1 and 12, —(C=O)SC$_n$H$_{2n+1}$ with n between 1 and 30, preferably between 1 and 12, -nitrobenzene, -benzyl, -halobenzyl, -amide, -carbonate, -benzoyl, -peroxyl, -nitrile, -thiol, -imide, -carbamate, -cyanate, -alkyne, -phenyl, -halophenyl, -picolyl,
M, which is optionally present, is a group covalently bonded to Q and to Z, M being chosen from alkyl, alkenyl, alkyne, aryl, alkylaryl, heteroaryl, acyl, alkyloxy, alkylamino, alkoxyamino, amido, alkylimido, alkenylimido, arylimido, fluoroalkyl, alkylphosphate, alkylthio, thioacyl, alkylsulfonyl, arylsulfonyl, alkylsulfinyl, alkylammonium, alkylsulfonium, alkylsilyl, alkylcarbonyl, alkylcarbanyl, alkylcarbamoyl or alkylhydroxylamino, Z is a cleavable group, chosen from —O—, —S—, =SH—, =S=, ≡S—, —SiH$_2$—, =SiH—, =Si=, ≡Si—, —SeH—, ≡Se—, =Se=, —SeH$_2$—, —PH—, =P—, =PH=, ≡P=, ≡PH=, —PH$_3$—, —AsH—, =As—, =AsH=, ≡As=, ≡AsH—, -ASH$_3$—, amine, ester, silyl, alkyl, benzyl, nitrobenzyl, amide, carbonate, benzoyl, peroxyl, nitrile, thiol, imide, carbamate, cyanate, hydroxylamine, sulfoxide, sulfonate, thiosulfinate, thioester, acyl halide, hypoiodyl, alkyne, halophenyl, halobenzyl, picoyl, diol or disulfide, or chosen from —CH$_2$ or —NH— when M is a -nitrobenzyl-, a -nitrotolyl-, a -nitroxylyl-, a -nitronaphthyl- or a -nitrophenyl-, Q is an end functional, or effector, group of the R or R' group, Q being chosen from biotin, a protein, a polynucleotide of defined sequence, a carbohydrate, an antigen, a hormone, a neurotransmitter, a glycoside such as digoxin, a sulfur-containing radical, in particular bearing a thiol function, such as glutathione, or a bidentate ligand such as catechol, R and R' possibly being present independently or simultaneously, and when R and R' are present simultaneously:
the Z groups may be identical or different,
the M groups may be identical or different,
the Q groups may be identical or different,
"base" represents a "natural" nitrogenous base chosen from adenine, thymine, cytosine, guanine or uracil or a natural nitrogenous base analog, with the exception of thymine when R' is present and Q comprises biotin.

Preferably, T, when it is not hydrogen, and also R and R', constitute groups which provide the chain termination of the elongation step of a nucleic acid synthesis process.

The term "cleavable radical or group" is intended to mean a radical or a group covalently bonded to the oxygen in position 3' or 2' of the ribose molecule or in position 3' of the deoxyribose molecule, or to an atom of the nitrogenous base, it being possible for said bond to be broken chemically or photochemically. Advantageously, the breaking of all of the bonds of the cleavable radicals or groups T and Z of the nucleotide molecule according to the invention is carried out entirely and simultaneously, that is to say during the same "deprotection" step, in particular by application of one and the same condition or by the combined action of one and the same reagent.

This deletion of the modifier groups is preferably total in order to result in the generation of a nucleotide free of any modifier group, that is to say identical to a natural nucleotide (except for the structure of the nitrogenous base).

As previously indicated, the R and R' groups are groups which advantageously provide the chain ending of the elongation step of a nucleic acid synthesis process. These R and R' groups can have properties, by means of the functional group Q placed at the free end of R and R', of attachment to another molecule, different than a nucleic acid, for example a molecule present on a support.

This is because, during the nucleic acid synthesis process, for example in the process described in FR 14-53455 mentioned above, some steps assume that the modified nucleotides used can interact with solid supports. These solid supports comprise, at their surface, molecules, proteins or chemical functions that are compatible with the modifier groups of the present nucleotides. This functionality of the modified nucleotides is then essential for the nucleic acid synthesis process to take place correctly. In one preferred embodiment, the modified nucleotides comprise a group which allows them to become combined with a solid support in order to be purified, for example, by forming, with the molecules present at the surface of a solid support, combination complexes having a very low dissociation constant, in particular less than $10^{-6}$ mol/l. Following the deprotection step, the group providing this combination function is then capable of being destroyed, thus eliminating the interaction between the nucleotide and the solid support. In this case, the nucleotide according to the invention has a double advantage, namely the presence of a group allowing purification and the capacity for destruction of this same group simultaneously with the other modifier groups, on one and the same nucleotide.

Preferably, the modifier group R is borne by the nitrogenous base and forms one of the structures (V) below:

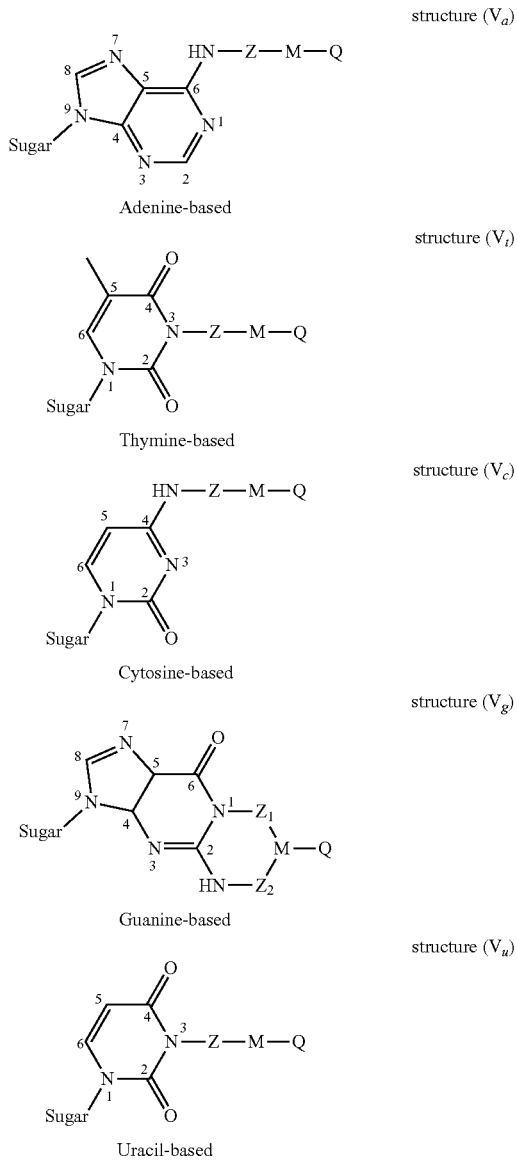

in which structures:
"sugar" represents the bond between said nitrogenous base and the ribose or deoxyribose molecule of the nucleotide molecule,
$Z_1$ and $Z_2$ are identical or different cleavable Z groups.
The Z, M and Q groups have the meanings previously described.

In this embodiment of the invention, the nucleotides are modified with groups borne by the atoms of the nitrogenous bases usually involved in Watson-Crick pairing mechanisms, that is to say borne by the nitrogen atoms of the amine functions normally involved in the pairing with a complementary nucleotide. The attachment of the various modifier groups to the atoms consisting the nitrogenous bases is always carried out by means of the Z groups, of cleavable type, via a bond of covalent type.

In the case of a nitrogenous base of adenine type, one preferred embodiment of the present invention consists in bonding the modifier group to the primary amine group 6-$NH_2$ (structure $V_a$).

In the case of a nitrogenous base of thymine type, another preferred embodiment of the present invention consists in bonding the modifier group to the secondary amine group 3-NH (structure $V_t$).

In the case of a nitrogenous base of cytosine type, another preferred embodiment of the present invention consists in bonding the modifier group to the primary amine group 4-$NH_2$ (structure $V_c$).

In the case of a nitrogenous base of uracil type, another preferred embodiment of the invention consists in bonding the modifier group to the secondary amine group 3-NH (structure $V_u$).

In the case of a nitrogenous base of guanine type, another preferred embodiment of the present invention consists in bonding the modifier group to one of the two, or simultaneously to both, amine groups, one being secondary 1-NH and the other primary 2-$NH_2$, by means of cleavable groups (structure $V_g$). In the particular case where the two amine groups 1-NH and 2-$NH_2$ are simultaneously used to bear the modifier groups, a ring, preferentially composed of 6 atoms, may occur between the various separating subgroups. This ring optionally brings about stabilization of the structure of the modifier groups.

In these embodiments where the modifier group is borne by the nitrogen base, the 3'OH and/or 2'OH sites of the nucleotides are free, promoting their use as substrates for the elongation enzymes during nucleic acid synthesis.

Intermolecular hydrogen bonds can occur. Indeed, the modifier group R borne by the nitrogenous base can form one of the structures (VI) below:

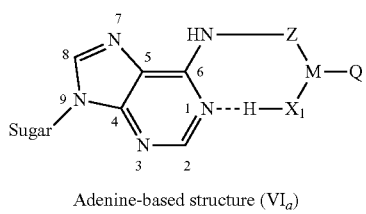

Adenine-based structure ($VI_a$)

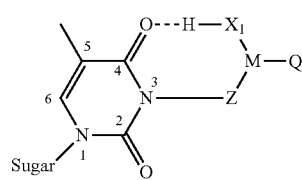

Thymine-based structure ($VI_t$)

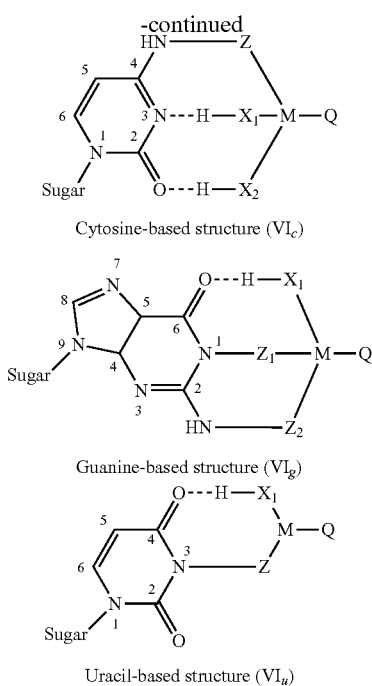

in which:

"Sugar" represents the bond between said nitrogenous base and the ribose or deoxyribose molecule of the nucleotide molecule, $X_1$ and $X_2$, which may be identical or different, represent nitrogen, oxygen or sulfur atoms borne by M and capable of forming, with said nitrogenous bases of the modified nucleotide, intramolecular hydrogen bonds (these hydrogen bonds are then similar to the intermolecular hydrogen bonds observed during conventional pairings between complementary nucleotides).

This configuration reinforces the stability of the modified nucleotides. It also influences the compactness of the modifier groups and allows their use by elongation enzymes that are usually dependent on the presence of a template strand.

In the case of a nitrogenous base of adenine type, one preferred embodiment of the present invention consists in bonding the modifier group to the primary amine group 6-$NH_2$ (structure $VI_a$). The $X_1$ group present promotes the creation of an intramolecular hydrogen bond with the nitrogen atom 1 of the purine ring. Thus, the presence of a complementary thymine is mimicked.

In the case of a nitrogenous base of thymine type, one preferred embodiment of the present invention consists in bonding the modifier group to the secondary amine group 3-NH (structure $VI_t$). The $X_1$ group present promotes the creation of an intramolecular hydrogen bond with the oxygen atom in position 4 of the pyrimidine ring. Thus, the presence of a complementary adenine is mimicked.

In the case of a nitrogenous base of cytosine type, one preferred embodiment of the present invention consists in bonding the modifier group to the primary amine group 4-$NH_2$ (structure $VI_c$). The $X_1$ and $X_2$ groups present promote the creation of intramolecular hydrogen bonds with the nitrogen atom in position 3 and the oxygen atom in position 2 of the pyrimidine ring. Thus, the presence of a complementary guanine is mimicked.

In the case of a nitrogenous base of guanine type, one preferred embodiment of the present invention consists in bonding the modifier group to the two amine groups, the first being secondary 1-NH and the second primary 2-$NH_2$ (structure $VI_g$), by means of cleavable $Z_1$ and $Z_2$ groups. The $X_1$ group present promotes the creation of the intramolecular hydrogen bond with the oxygen atom in position 6 of the purine ring. Thus, the presence of a complementary cytosine is mimicked.

In the case of a nitrogenous base of uracil type, one preferred embodiment of the invention consists in bonding the modifier group to the secondary amine group 3-NH (structure $VI_u$). The $X_1$ group present promotes the creation of a hydrogen bond with the oxygen in position 4 of the pyrimidine ring. Thus, the presence of a complementary adenine is mimicked.

It is not necessarily the mission of the modified nucleotides according to the present invention to pair with a possible complementary nucleotide borne by any template strand. During the use of the modified nucleotides which are subjects of the present invention, for the generation of nucleic acids, said nucleotides are not necessarily intended to be incorporated by complementary interaction with a possible template strand.

The modified nucleotides which are subjects of the present invention have characteristics which allow them to lose their modifier groups during specific steps. After the loss of all their modifier groups, the nucleotides of the present invention thus transformed then recover their ability to pair with complementary nucleotides borne by template strands.

According to one particular embodiment, the nucleotide according to the invention can then be used as a substrate for polymerases that are normally dependent on the presence of a template nucleic acid strand complementary to the strand undergoing synthesis, even in the absence of a complementary strand.

The functional end radical Q of the R or R' group is preferably capable of allowing, during nucleic acid synthesis, the attachment of said nucleotide to a solid support, by means of a molecule other than a nucleic acid, such as a protein, attached to the surface of said support, and more particularly capable of interacting with molecules other than a nucleic acid, according to one or another of the following interaction pairs: antigen/antibody, hormone/receptor, biotin/(strept)avidin, neurotransmitter/receptor, polymerase/promoter, digoxin/antidigoxin, carbohydrate/lectin, sulfur-containing radical/metal such as gold, glutathione/glutathione S-transferase, or else bidentate ligand/metal oxide.

The metal oxides may be, for example, $TiO_2$, $ZrO_2$, $CeO_2$, $Fe_3O_4$, $Ga_2O_3$, $In_2O_3$, $Cr_2O_3$, $Al_2O_3$, ZnO, CuO, $Cu_2O_3$, $Mn_3O_4$, $Nn_2O_3$, $V_2O_3$, $MoO_2$.

The bidentate ligands may be catechol, hydroxamate or a hydroxycarboxylate.

The T radical is termed "blocker" in that it protects the 3' hydroxyl group or the 2' hydroxyl group of the carbohydrate against any additional nucleotide addition.

Preferably, T and Z, or $Z_1$, $Z_2$ are cleavable, during nucleic acid synthesis, by irradiation of said nucleotide by means of electromagnetic radiation having a wavelength of between $10^{-3}$ and $10^{-11}$ meters, in particular by exposure to ultraviolet radiation.

Advantageous embodiments of the invention relate to the following nucleotides:

a nucleotide for which $X_1$ and $X_2$ are —NH, T is —$NH_2$, Z is —$CH_2$, M is methylnitrobenzyl-, and Q is -biotin, a nucleotide for which $X_1$ and $X_2$ are —NH, T is —$NH_2$, Z, $Z_1$ and $Z_2$ are each —O—, M is -nitronaphthyl- and Q is -biotin, a nucleotide of formula (I) bearing only the R' group in which: Z is —(C=O)—, M is —C$_8$H$_{16}$— and Q is —NH— biotinyl, a nucleotide of particular structure (V) in which Z, Z$_1$ and Z$_2$ are each —(COO)—, M is -tert-butylnitrobenzyl- and Q is —NH-biotinyl.

The present invention also relates to the use of nucleotides, as described previously, in a process for the production of genes, of synthetic nucleic acid sequences, of DNA, of RNA or of nucleic acid polymers, in particular according to an enzymatic synthesis process.

An advantageous use is for the incorporation of said nucleotide into a polynucleotide chain previously immobilized on a solid support, more particularly when the polynucleotide chain is attached via its 5' end and the incorporation of said nucleotide is carried out via the 3' end of the polynucleotide chain.

Nevertheless, the nucleotides according to the invention are in free form, in combination with a counterion if required. Although they have the capacity to attach to a solid support, these nucleotides are free from any support at the time of their incorporation into the polynucleotide chain. Their chemical structure is thus not linked to any solid support. The free nature of the modified nucleotides is particularly important for their use in the process described in the patent application, not yet published, FR 14-53455 since the nucleotides are added to fragments of nucleic acids which are themselves immobilized. These fragments are released and then, by virtue of the effector group of the nucleotides that have just been incorporated, are subsequently attached via the opposite end to a second solid support. These are thus complete nucleic acid chains, or polynucleotides, of desired sequence which are attached to a solid support, and not the nucleotides according to the invention, used to construct the polynucleotides.

The present invention also relates to a kit comprising at least one modified nucleotide according to the invention, more particularly said kit may comprise various modified nucleotides, an elongation enzyme and a solid support capable of attaching at least one of said nucleotides.

The present invention will be described in greater detail by means of the illustrative examples below in relation to the appended figures in which:

FIG. 1 shows the various general structures of the modified nucleotides which are subjects of the present invention;

FIG. 2 presents the particular structures of the modified nucleotides of formula (V);

FIG. 3 presents the formulae of the natural nitrogenous bases adenine, thymine, cytosine and guanine;

FIG. 10 shows an example of deprotection of the polymerized compound NH$_2$-dT-NitroB-Biot;

FIG. 11 shows an example of deprotection of the polymerized compound NH$_2$-dG-NitroB-Biot;

Figure 15:
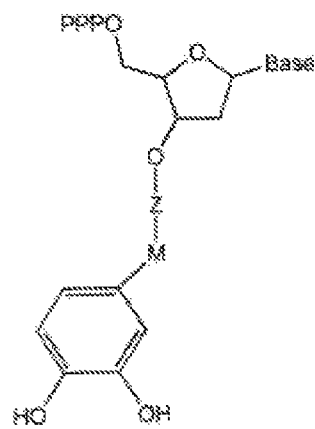
Figure 16:
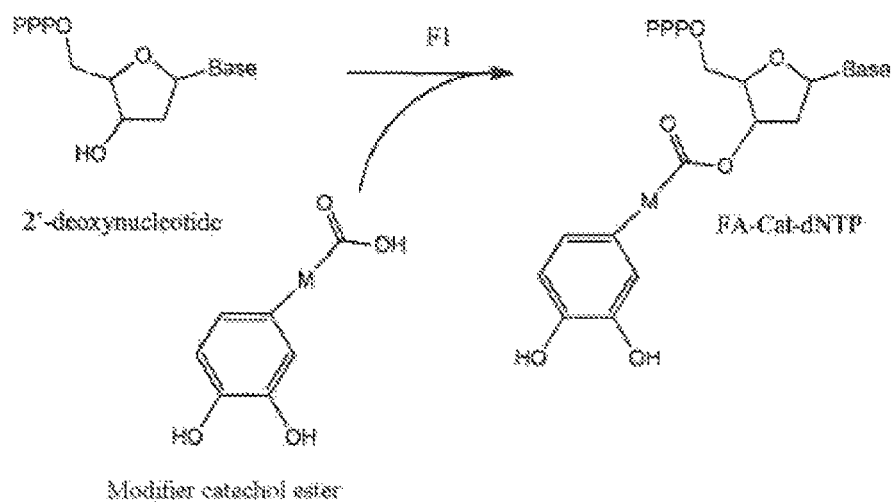

FIG. 15 presents an example of a modified nucleotide according to the present invention, the Q group being a catechol;

FIG. 16 represents diagrammatically the synthesis of the compound FA-Cat-dNTP.

EXAMPLES

Synthesis of Modified (Protected) Nucleotides
Illustrative Examples 1 to 6

Figure 2:
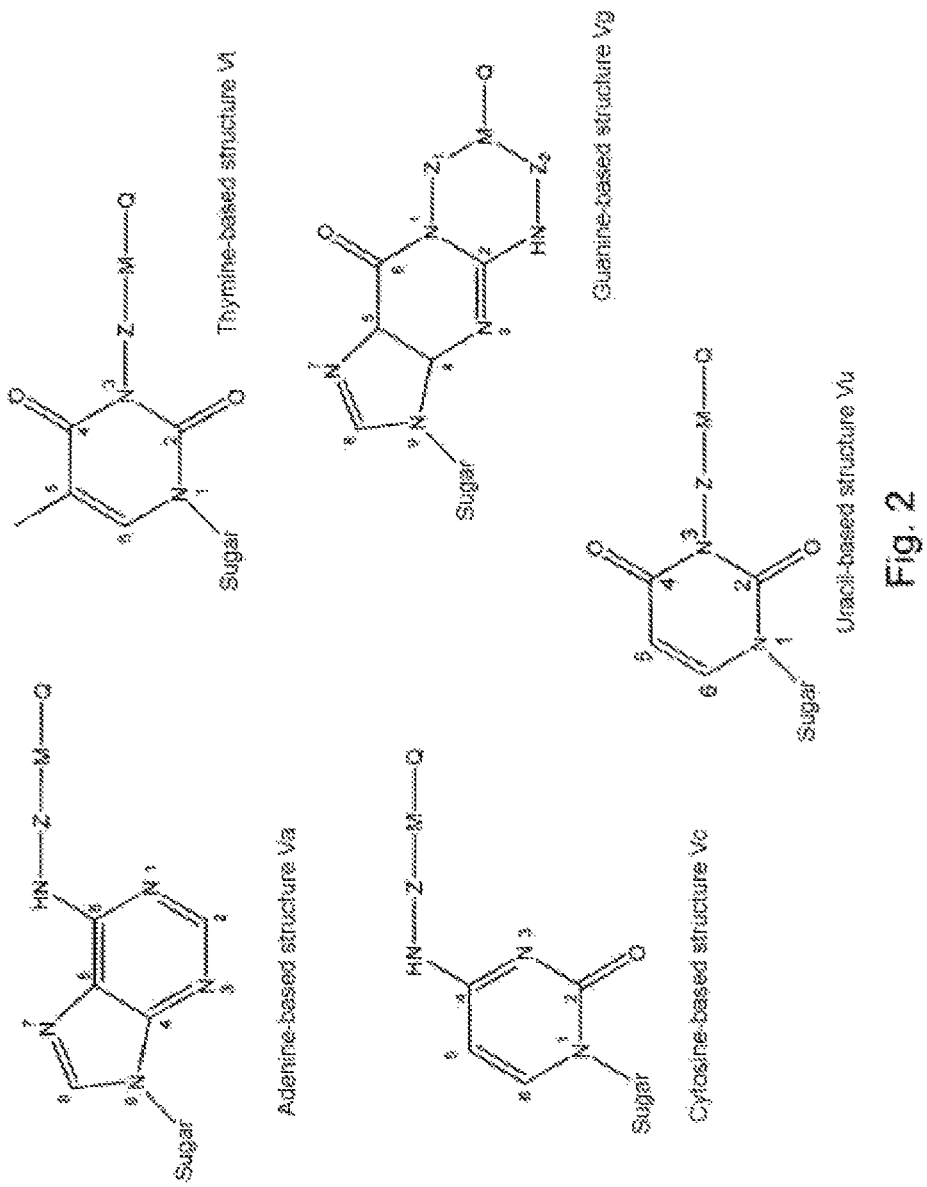
Figure 3:
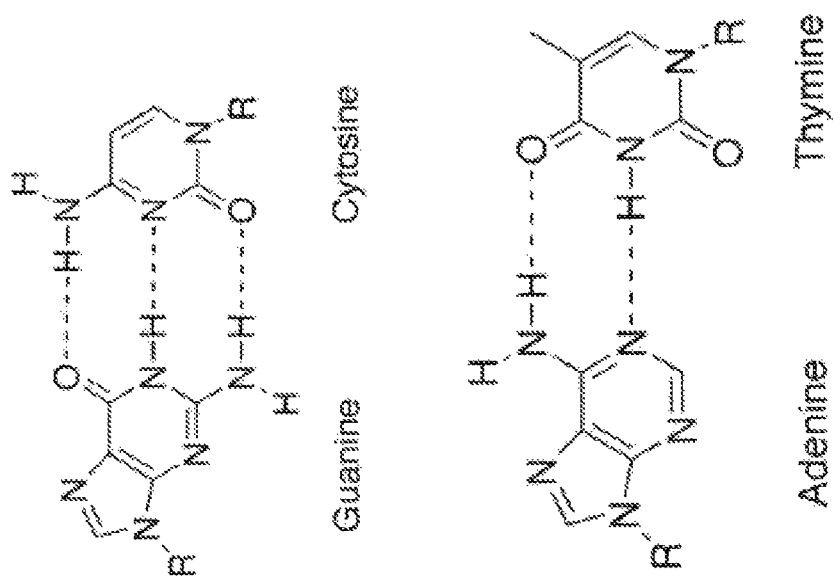
Figure 4:
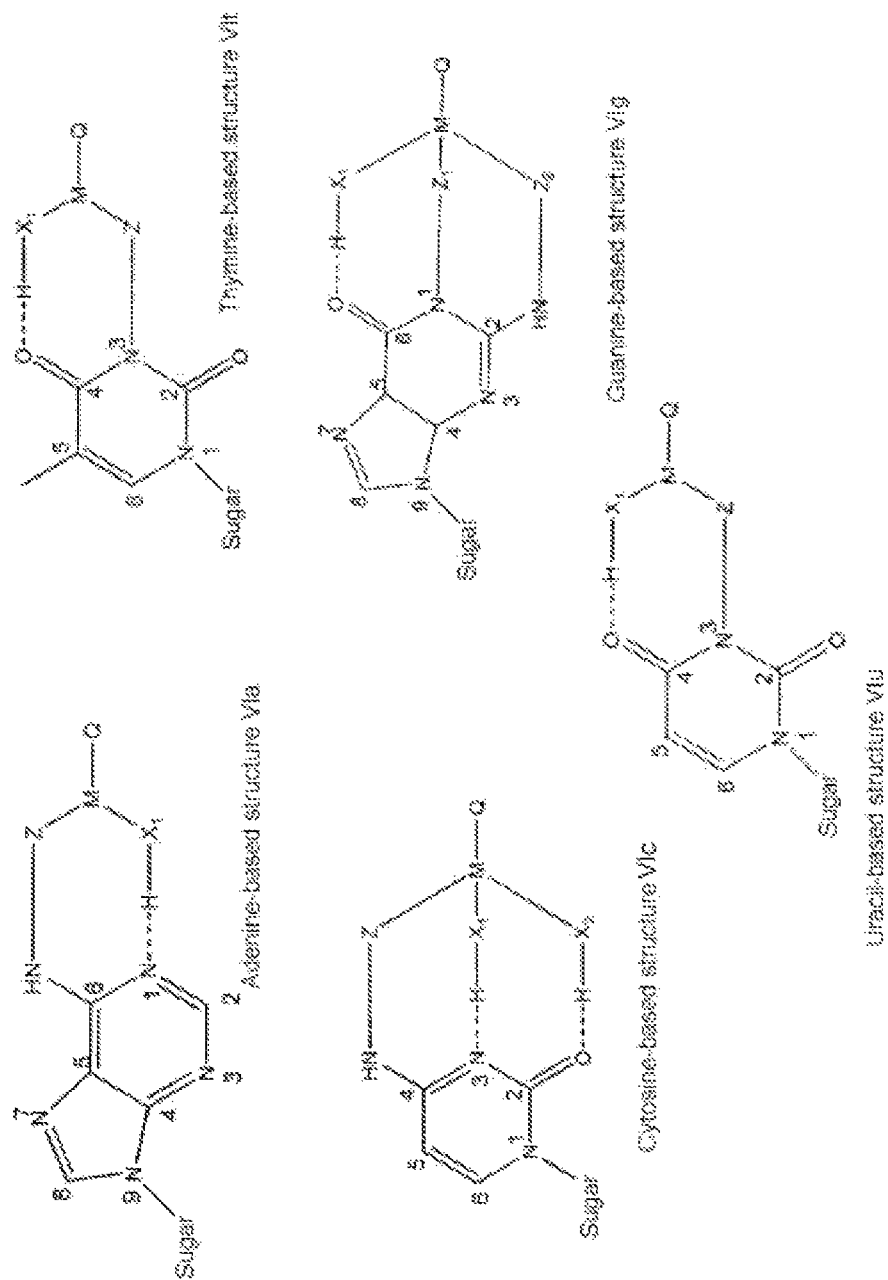
FIG. 4 shows examples of modifier groups capable of interactions of intramolecular hydrogen bond type, of formula (VI)
Figure 5:
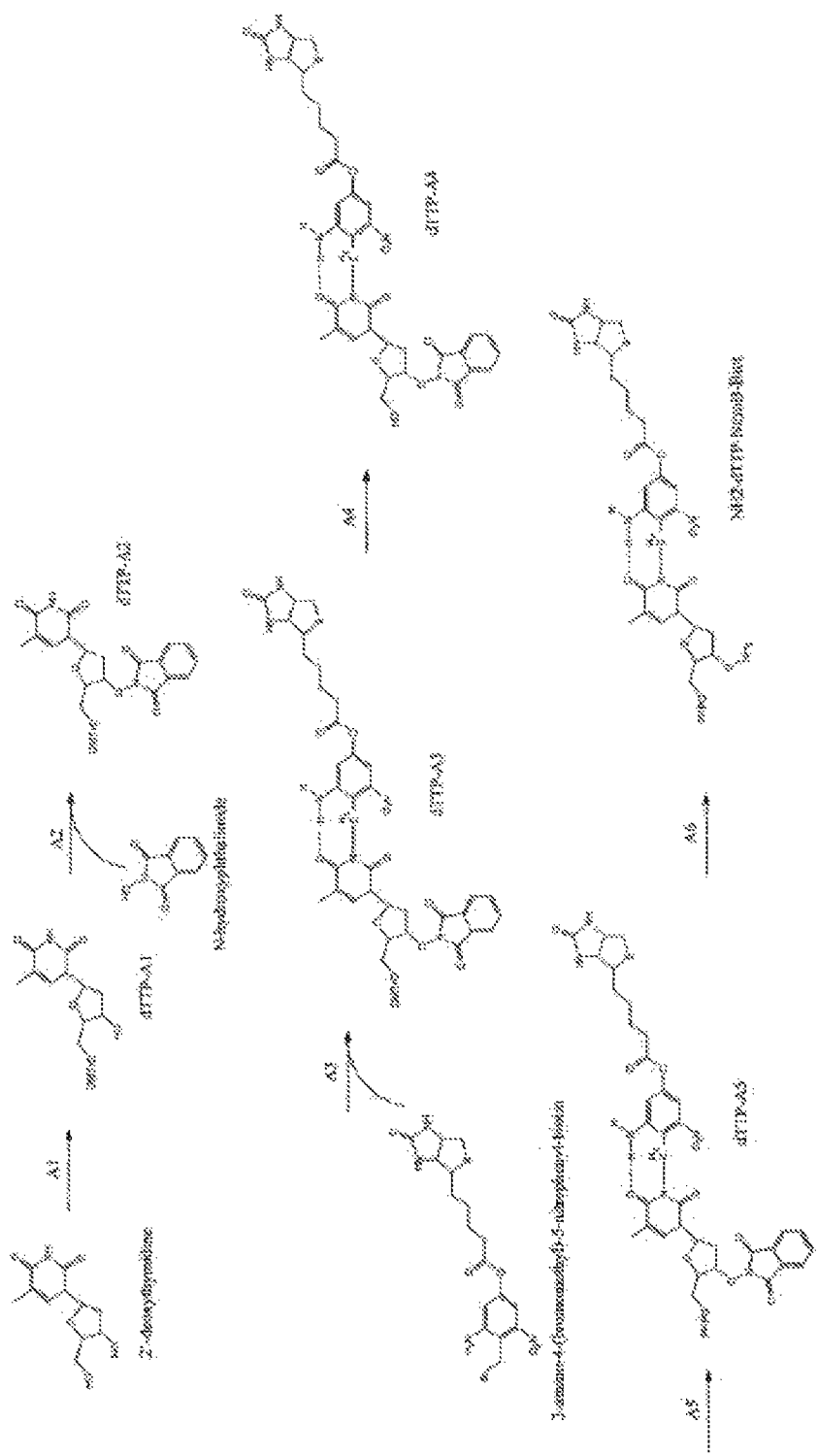
FIG. 5 represents diagrammatically the synthesis of the compound NH$_2$-dTTP-NitroB-Biot.

Example 1—Synthesis of the Compound
NH$_2$-dTTP-NitroB-Biot (FIG. 5)

Step A1: 2.2 ml of Et$_3$N (triethylamine) and 175 mg of DMAP (4-dimethylaminopyridine) and then 5.25 g of DMTCl (4,4'-dimethoxytrityl chloride) are added, at ambient temperature overnight, to 5 g of 2'-deoxythymidine dissolved in pyridine. 2.4 ml of Et$_3$N and 1.27 ml of MsCl (methanesulfonyl chloride) are then added to the mixture. After incubation for 2 h at ambient temperature, the mixture is filtered and washed with ethyl acetate. The filtrate is concentrated and dissolved in 75 ml of ethanol, to which 1M of NaOH is added. After refluxing for 1.5 h, the mixture is cooled to ambient temperature and 1M of HCl is added. The ethanol is evaporated off in a rotary evaporator and the residue is extracted with CH$_2$Cl$_2$. After silica gel column purification, the product dTTP-A1 is obtained.

Step A2: 1.75 ml of N,N'-diisopropyl azodicarboxylate are added, at 0° C., to a solution of 2.237 mmol of product dTTP-A1, 2.1 g of triphenylphosphine and 1.3 g of N-hydroxyphthalimide in 50 ml of tetrahydrofuran. After reheating at ambient temperature overnight, the reaction product is treated with: 0.3 ml of water and the solvent is evaporated off under vacuum. Most of the impurities are eliminated by chromatography, then giving the product dTT-A2.

Step A3: 10 equivalents of LiH in DMF are added, at ambient temperature, to one equivalent of compound dTT-A2. The mixture reacts for 30 min. The reaction is continued by adding 3-amino-4-(bromomethyl)-5-nitrophenylbiotin, and then the mixture is stirred for several hours. The product dTT-A3 is obtained.

Step A4: The compound dTTP-A3 is resuspended in methanol and treated with aqueous concentrated hydrochloric acid. The solution is cooled to −20° C. overnight, resulting in the product dTTP-A4.

Step A5: A solution of 130 mg of 2-chloro-4H-1,2,3-benzodioxaphosphorin-4-one in 1.3 ml of dioxane is added to 425 mg of 5'-OH nucleoside analog dTTP-A4 dissolved in 2 ml of pyridine and 1.7 ml of dioxane. The mixture is left at ambient temperature for 20 min. A mixture of 1.4 mmol of tributylammonium pyrophosphate in DMF and 3.2 mmol of tributylamine is added. After 20 min, a solution of 180 mg of iodine and 0.28 ml of water in 14 ml of pyridine is added. After 30 min, the reaction is stopped by adding an aqueous 5% Na$_2$SO$_3$ solution. The solvents are evaporated off under vacuum. 25 ml of water and 20 ml of CH$_3$CN are added. The mixture is filtered and purified by reverse-phase HPLC to give a triphosphate compound, in the case in point dTTP-A5.

Step A6: 0.385 ml of cold methylhydrazine is added to 3.725 mmol of compound dTTP-A5 in anhydrous $CH_3Cl_2$ at −5° C. After 10 min, a precipitate of 1,2-dihydro-4-hydroxy-2-methyl-1-oxophthalizine is formed. The mixture is stirred for 1 h at ambient temperature. The precipitate is removed by filtration and washed with $CH_2Cl_2$. The filtrate is then concentrated in a rotary evaporator and purified by chromatography to give the product $NH_2$-dTTP-NitroN-Biot.

Figure 6:
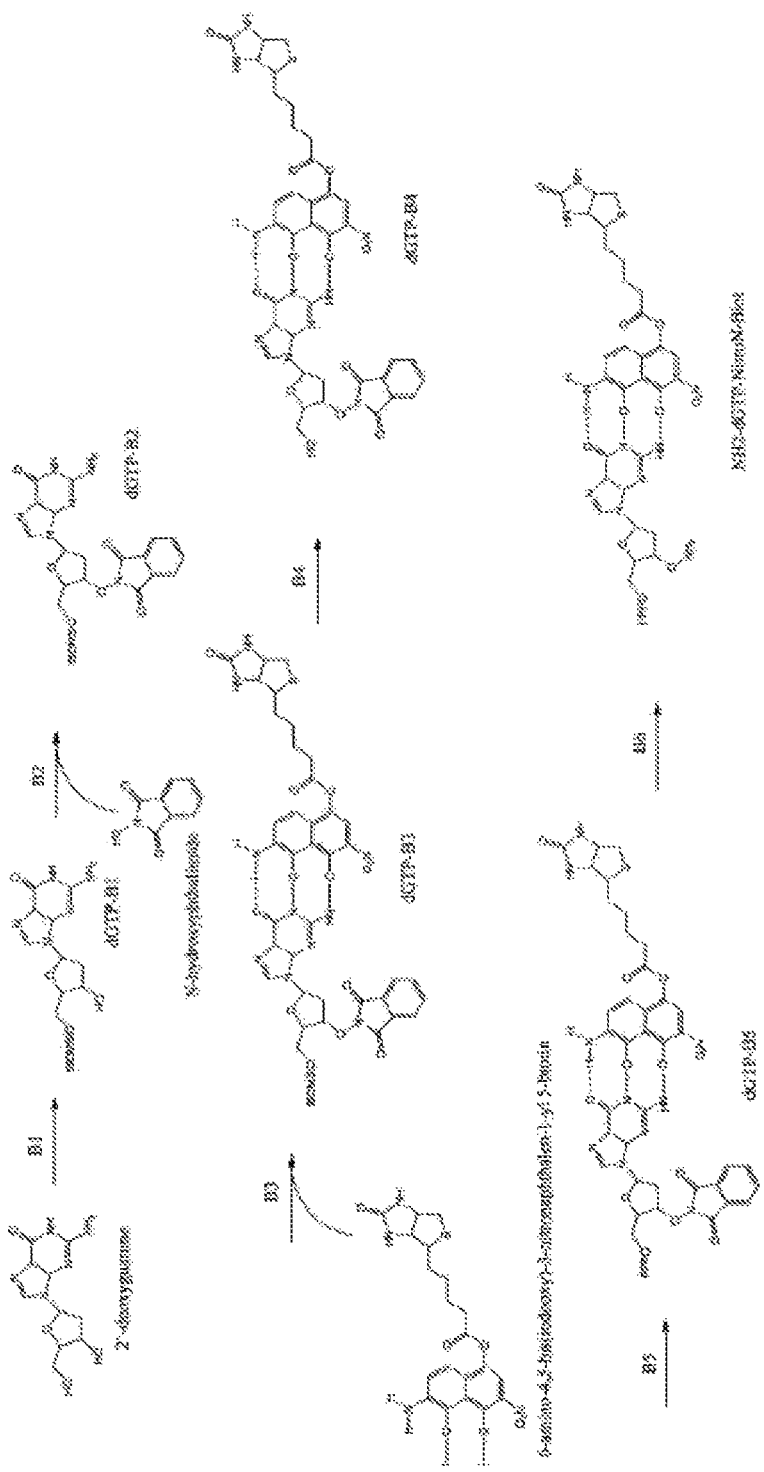
FIG. 6 represents diagrammatically the synthesis of the compound NH$_2$-dGTP-NitroN-Biot.

Example 2—Synthesis of the Compound $NH_2$-dGTP-NitroN-Biot (FIG. 6)

Step B1: 2.4 mmol of tert-butyldimethylsilyl chloride are added to a stirred solution of 1.845 mmol of 2'-deoxyguanine and 326 mg of imidazole in anhydrous DMF. The reaction is incubated with stirring at ambient temperature for 20 h. The solvents are removed under vacuum and the residue is purified by chromatography to give the product dGTP-B1.

Step B2: 1.75 ml of N,N'-diisopropyl azodicarboxylate are added, at 0° C., to a solution of 2.237 mmol of product dGTP-B1, 2.1 g of triphenylphosphine and 1.3 g of N-hydroxyphthalimide in 50 ml of tetrahydrofuran. After reheating at ambient temperature overnight, the reaction product is treated with 0.3 ml of water and the solvent is evaporated off under vacuum. Most of the impurities are removed by chromatography, then giving the product dGTP-B2.

Step B3: 3.785 mmol of compound dGTP-B2 are dried several times using 10 ml of pyridine and evaporation under vacuum. The residue is dissolved in 12.5 ml of $CH_2Cl_2$. 9 mmol of diisopropylethylamine and 7.57 mmol of 6-amino-4,5-bis(iodooxy)-3-nitronaphthalen-1-yl-5-biotin are added. When the reaction is complete, the mixture is diluted in 100 ml of $CH_2Cl_2$, and the organic phase is washed with 50 ml of sodium bicarbonate and 50 ml of water. It is then dried over sodium sulfate. The solvents are evaporated off under vacuum and the product is purified by chromatography to give dGTP-B3.

Step B4: 3.75 mmol of compound dGTP-B3 are dissolved in 20 ml of THF and treated with 1M of TBAF (tetra-n-butylammonium fluoride) in THF. The reaction is complete after approximately 2 h with stirring. The mixture is extracted with $CH_2Cl_2$ and purified by chromatography to give dGTP-B4.

Step B5: 425 mg of 5'-OH nucleoside analog are treated similarly to step A5 of example 1. The final mixture is filtered and purified by reverse-phase HPLC to give a triphosphate compound, in the case in point dGTP-B5.

Step B6: 0.385 ml of cold methylhydrazine is added to 3.725 mmol of compound dGTP-B5 in anhydrous $CH_2Cl_2$ at −5° C. After 10 min, a precipitate of 1,2-dihydro-4-hydroxy-2-methyl-1-oxophthalizine is formed. The mixture is stirred for 1 h at ambient temperature. The precipitate is removed by filtration and washed with $CH_2Cl_2$. The filtrate is then concentrated in a rotary evaporator and purified by chromatography to give the product $NH_2$-dGTP-NitroN-Biot.

Figure 7:
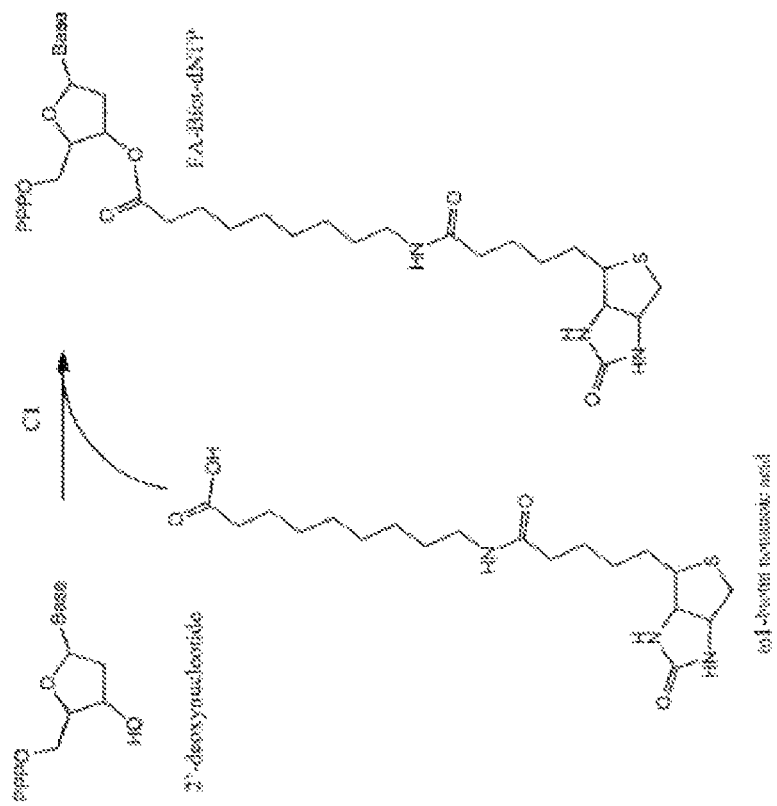
FIG. 7 represents diagrammatically the synthesis of the compounds FA-Biot-dNTP.

Example 3—Synthesis of the Compounds FA-Biot-dNTP (FIG. 7)

Step C1: 100 µl of 1M ω1-biotin nonanoic acid in DMF are mixed with 100 µl of 1M carbonyldiimidazole in DMF. The formation of imidazolide takes place in 30 s at ambient temperature. 100 µl of 50 mM dioxyribo-nucleotide 5'-triphosphate in water are then added to the mixture. The product is formed in 12 h at ambient temperature. It is then precipitated with acetone and dissolved in water so as to be finally purified by chromatography to give the product FA-Biot-dNTP.

Figure 8:
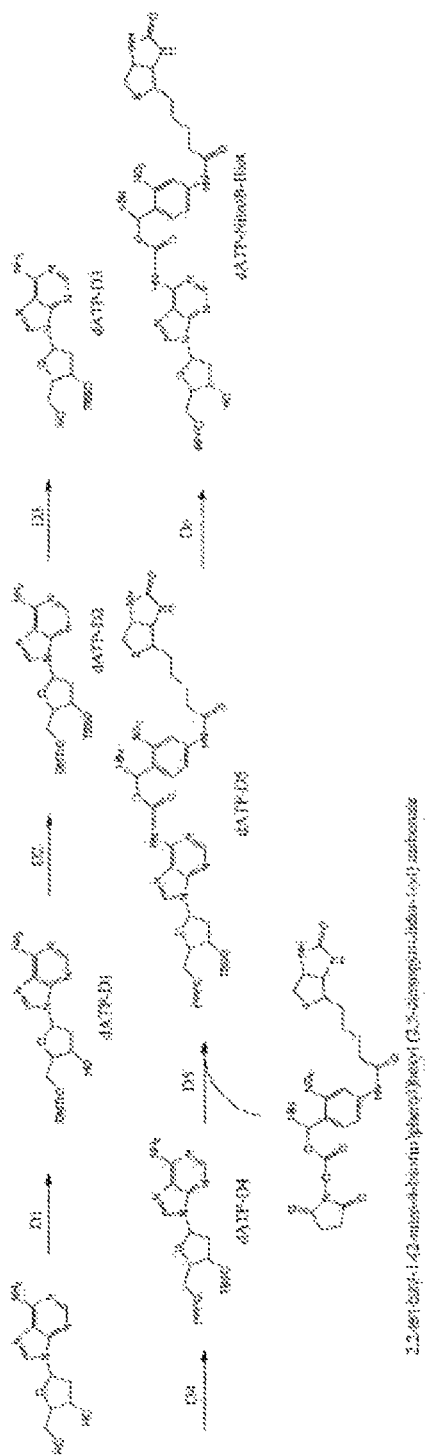
FIG. 8 represents diagrammatically the synthesis of the compound dATP-NitroB-Biot.

Example 4—Synthesis of the Compound dATP-NitroB-Biot (FIG. 8)

Step D1: 2.2 ml of $Et_3N$ and 175 mg of DMAP and then 5.25 g of DMTCl are added, at ambient temperature overnight, to 5 g of 2'-deoxyadenine dissolved in pyridine. 2.4 ml of $Et_3N$ and 1.27 ml of MsCl are then added to the mixture. After incubation for 2 h at ambient temperature, the mixture is filtered and washed with ethyl acetate. The filtrate is concentrated and dissolved in 75 ml of ethanol, to which is added 1M of NaOH. After refluxing for 1.5 h, the mixture is cooled to ambient temperature and 1M of HCl is added. The ethanol is evaporated off in a rotary evaporator and the residue is extracted with $CH_2Cl_2$. After silica gel column purification, the product dATP-D1 is obtained.

Step D2: 2.4 mmol of tert-butyldimethylsilyl chloride are added to a stirred solution of 1.845 mmol of dATP-D1 and 326 mg of imidazole in anhydrous DMF. The reaction is incubated with stirring at ambient temperature for 20 h. The solvents are removed by applying a vacuum and the residue is purified by chromatography to give the product dATP-D2.

Step D3: The compound dATP-D2 is resuspended in methanol and treated with aqueous concentrated hydrochloric acid. The solution is cooled to −20° C. overnight, resulting in the product dATP-D3.

Step D4: 425 mg of 5'-OH nucleoside analog are treated similarly to step A5 of example 1. The final mixture is filtered and purified by reverse-phase HPLC to give a triphosphate compound, in the case in point dATP-D4.

Step D5: 3.1 µmol of the compound dATP-D4 in 200 µl of 0.1M $NaHCO_3$, pH 8.0, are mixed with 3.4 µmol of 2,2-tert-butyl-1-(2-nitro-4-biotin)phenyl)hexyl (2,5-dioxopyrrolidin-1-yl) carbonate in 200 µl of dimethylformamide. The reaction is carried out at ambient temperature overnight to give dATP-D5 (Olejnik et al., PNAS, 1995, Vol 92, 7590-7594).

Step D6: 3.75 mmol of the compound dATP-D5 are dissolved in 20 ml of THF and treated with 1M of TBAF (tetra-n-butylammonium fluoride) in THF. The reaction is complete after approximately 2 h with stirring. The mixture is extracted with $CH_2Cl_2$ and purified by chromatography to give dATP-NitroB-Biot.

Figure 9:
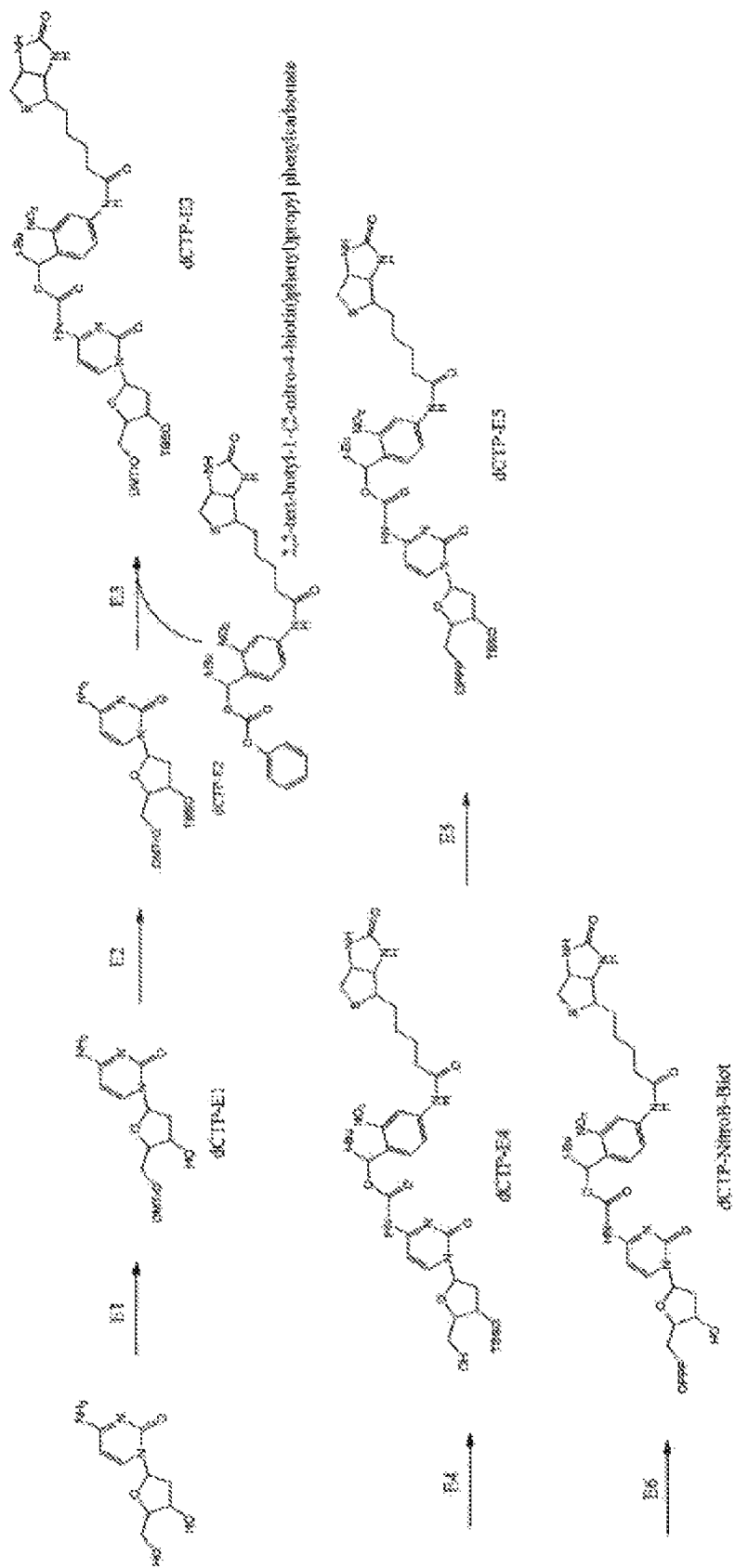
FIG. 9 represents diagrammatically the synthesis of the compound dCTP-NitroB-Biot.

Example 5—Synthesis of the Compound dCTP-NitroB-Biot (FIG. 9)

Step E1: 2.2 ml of $Et_3N$ and 175 mg of DMAP and then 5.25 g of DMTCl are added, at ambient temperature, overnight, to 5 g of 2'-deoxycytidine dissolved in pyridine. 2.4 ml of $Et_3N$ and 1.27 ml of MsCl are then added to the mixture. After incubation for 2 h at ambient temperature, the mixture is filtered and washed with ethyl acetate. The filtrate is concentrated and dissolved in 75 ml of ethanol, to which is added 1M of NaOH. After refluxing for 1.5 h, the mixture is cooled to ambient temperature and 1M of HCl is added. The ethanol is evaporated off in a rotary evaporator and the residue is extracted with $CH_2Cl_2$. After silica gel column purification, the product dCTP-E1 is obtained.

Step E2: 2.4 mmol of tert-butyldimethylsilyl chloride are added to a stirred solution of 1.845 mmol of dCTP-E1 and 326 mg of imidazole in anhydrous DMF. The reaction is incubated with stirring at ambient temperature for 20 h. The solvents are removed by applying a vacuum and the residue is purified by chromatography to give the product dCTP-E2.

Step E3: The compound dCTP-E2 is dissolved in absolute ethanol and cooled to 0° C. An equimolar solution of 2,2-tert-butyl-1-(2-nitro-4-biotin)phenyl)propylphenyl carbonate in absolute ethanol is added dropwise. The mixture is stirred at ambient temperature overnight. The solution is filtered, washed with water and extracted with $CH_2Cl_2$ to give dCTP-E3.

Step E4: The compound dCTP-E3 is resuspended in methanol and treated with aqueous concentrated hydrochloric acid. The solution is cooled to −20° C. overnight, resulting in the product dCTP-E4.

Step E5: 425 mg of 5'-OH nucleoside analog are treated similarly to step A5 of example 1. The final mixture is filtered and purified by reverse-phase HPLC to give a triphosphate compound, in the case in point dCTP-E5.

Step E6: 3.75 mmol of the compound dCTP-E5 are dissolved in 20 ml of THF and treated with 1M of TBAF (tetra-n-butylammonium fluoride) in THF. The reaction is complete after approximately 2 h with stirring. The mixture is extracted with $CH_2Cl_2$ and purified by chromatography to give dCTP-NitroB-Biot.

Example 6—Synthesis of the Compounds FA-Cat-dNTP (FIG. 16)

Step F1: 100 μl of 1M of modifier catechol ester in DMF are mixed with 110 μl of 1M dicyclohexylcarbodiimide (DCC) and 5 μl of 100% 4-(dimethylamino)pyridine in DMF. The mixture is incubated at 0° C. for 5 min. 500 μl of 50 mM deoxyribonucleotide 5'-triphosphate in DMF are then added to the mixture. The product is formed in 3 h at ambient temperature. It is then precipitated with acetone and dissolved in water so as to be finally purified by chromatography to give the product FA-Cat-dNTP.

Deprotection

After the addition of the nucleotide to a nucleic acid chain, the following examples 7 to 11 illustrate embodiments of the deprotection of said molecule, that is to say the removal of the modifier group(s).

Example 7—Deprotection of the Polymerized Nucleotides $NH_2$-dT-NitroB-Biot (FIG. 10)

The cleavage of the various modifier groups is carried out simultaneously during the following process. 20 mM of compound $NH_2$-dT-NitroB-Biot in aqueous solution are treated with a solution comprising 350 to 700 mM of $NaNO_2$ and 1M NaOAc, pH 5.5. After incubation for 1 to 2 min at ambient temperature exposed to UV light having a wavelength of 365 nm, the reaction is stopped by adding 1M phosphate buffer, pH 7.0, and stopping the illumination. The deprotection reaction product is dT.

Example 8—Deprotection of the Polymerized Nucleotides $NH_2$-dG-NitroN-Biot (FIG. 11)

The cleavage of the various modifier groups is carried out simultaneously during the following process: 20 mM of compound $NH_2$-dG-NitroN-Biot in aqueous solution are treated with a solution comprising 350 to 700 mM of $NaNO_2$ and 1M NaOAc, pH 5.5. After 1 to 2 min of incubation at ambient temperature exposed to UV light having a wavelength of 365 nm, the reaction is stopped by adding 1M phosphate buffer, pH 7.0, and stopping the illumination. The deprotection reaction product is dG.

Figure 12:
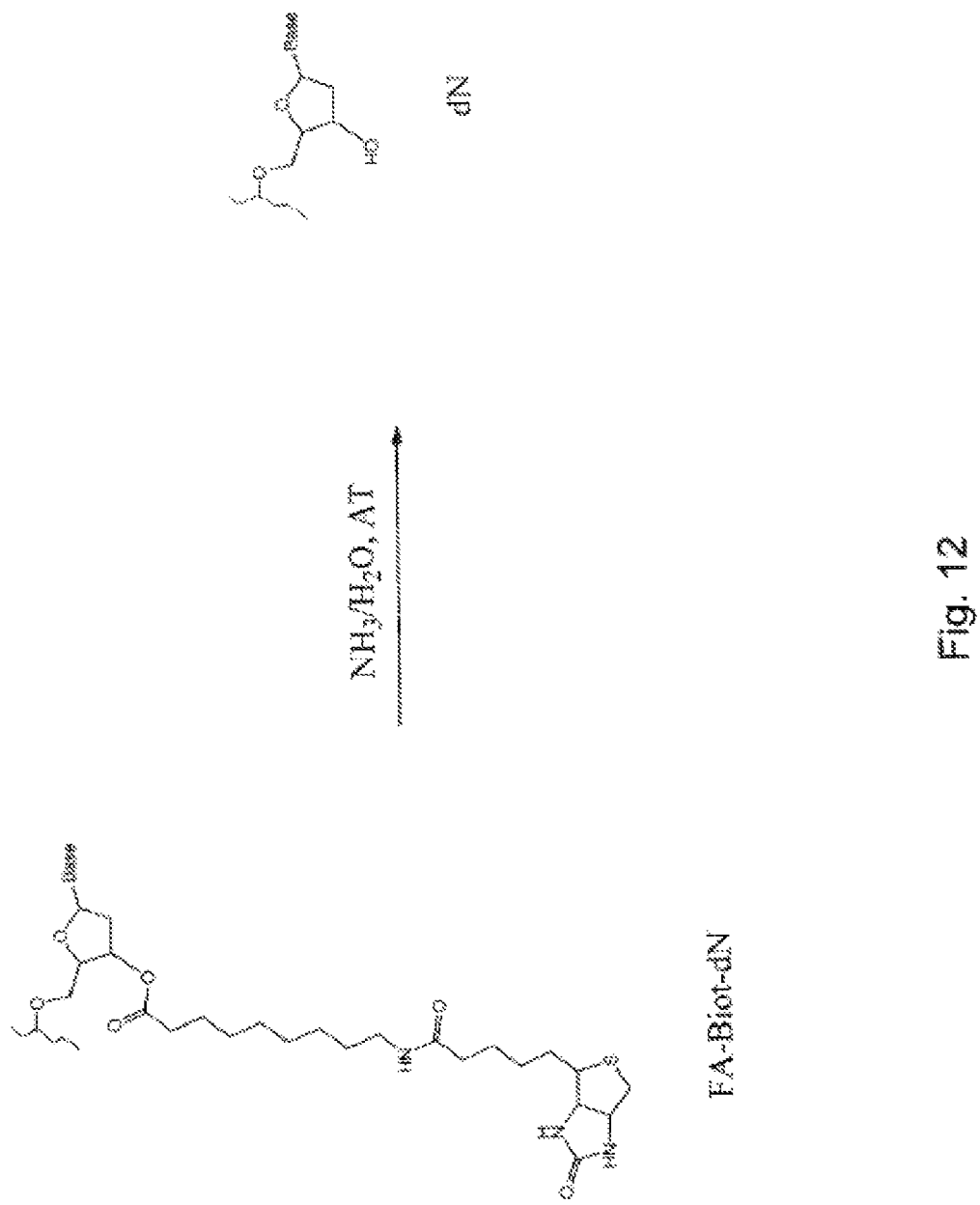
FIG. 12 shows an example of deprotection of the polymerized compound FA-Biot-dNTP.

Example 9—Deprotection of the Polymerized Nucleotides of FA-Biot-dN Type (FIG. 12)

The cleavage of the modifier groups borne by the 3'-OH end is carried out by hydrolysis of the ester function with an aqueous ammonia solution, 1 to 100 mM, at ambient temperature for 1 h. The product obtained is of dN type.

Figure 13:
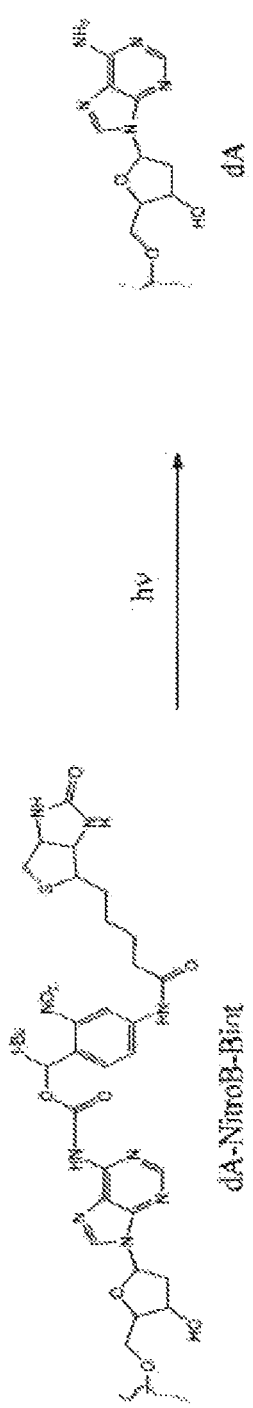
FIG. 13 shows an example of deprotection by photocleavage of the polymerized compound dA-NitroB-Biot.

Example 10—Deprotection of the Polymerized Nucleotides dA-NitroB-Biot by Photocleavage (FIG. 13)

The cleavage of the modifier groups borne on the nitrogenous base is carried out by photocleavage. The compound dA-NitroB-Biot is exposed to a UV source having a wavelength of 300 to 370 nm at ambient temperature. The UV source is stopped after 30 to 300 seconds to give the product dA.

Figure 14:
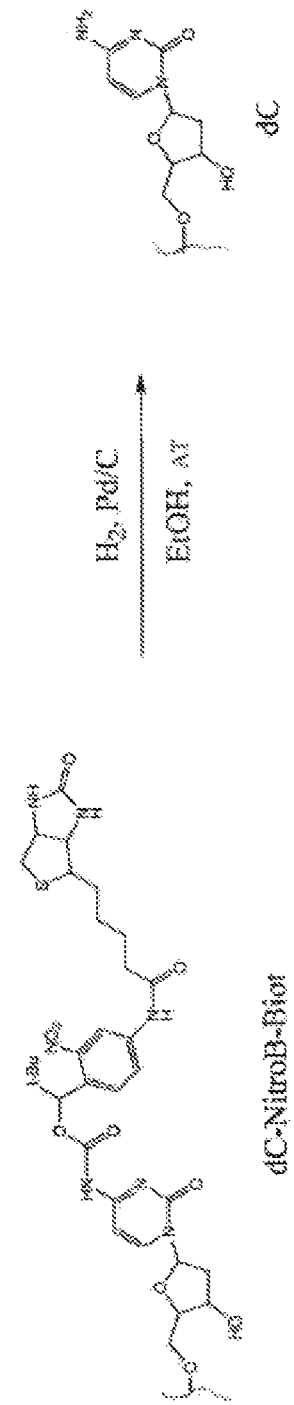
FIG. 14 shows an example of deprotection by chemical cleavage of the polymerized compound dC-NitroB-Biot.

Example 11—Deprotection of the Polymerized Nucleotides dC-NitroB-Biol by Chemical Cleavage (FIG. 14)

The cleavage of the modifier groups borne on the nitrogenous base is carried out by chemical cleavage. 0.01 mmol of compound dC-NitroB-Biot is dissolved in 0.1 ml of ethanol. A solution of 0.02 mmol of sodium tetrachloropalladate II dissolved in ethanol is added. Dihydrogen gas is bubbled into the mixture with stirring for 20 min. The product obtained is dC.

A similar procedure is described by Kobayashi et al. (Science, 2004, 304, 1305-1308) using immobilized palladium, and a stream of $H_2$ of 1 ml/min in THF can be used as a variant.

Example 12—Use of Nucleotides According to the Invention for a Nucleic Acid Synthesis The modified nucleotides which are the subject of the present invention can be advantageously used to carry out the enzymatic synthesis of nucleic acids without the presence of template strands according to the process described in patent application FR. 14-53455. The enzyme chosen for carrying out the step of adding the modified nucleotides is the commercially available terminal deoxynucleotidyl transferase or TdT.

The primer used to initiate the synthesis is given below:

```
                                              Seq No 1
          5'-AGCCAAGCGGTCGCGATGAT-3'
```

The modified nucleotides used are $NH_2$-dTTP-NitroB-Biot prepared according to example 1. They make it possible to add a T to the sequence No. 1 presented. It is expected that only one nucleotide will be added to each DNA fragment during each elongation step, as described below.

A glass plate bearing "capture" fragments having the following sequence:

```
                                              Seq No 2
             5'-GTCCGCTTGGCT-3'
``` attached to this glass plate by their 3' end, is used to capture the primers of sequence 1. This glass plate constitutes the base of a parallelepipedal reaction chamber having a volume of 50 μl. The capture is carried out using a buffer solution comprising: 20 mM Tris-HCl (pH=7.5), 500 mM LiCl and 1 mM EDTA to which are added 2 pmol of primer. The capture step is carried out over the course of 30 min at ambient temperature. Once the primers have been captured, the plate is washed by adding and removing three times 50 μl of the following buffer solution: 20 mM Tris-HCl (pH=7.5), 200 mM LiCl and 1 mM EDTA.

The synthesis begins with the addition of the following reagents to the reaction chamber: 50 U of TdT, 1 M of potassium cacodylate, 125 mM of Tris-HCl, 0.05% (v/v) of Triton X-100, 5 mM of $CoCl_2$, at pH 7.2. Next are added 100 μM of $NH_2$-dTTP-NitroB-Biot nucleotides which are free and in solution with their counterions. The enzyme at 2 μM is finally added in order to start the addition reaction. The total reaction volume is 50 μl. The mixture is incubated for 5 min at 37° C.

Once the synthesis reaction has been completed, the plate is washed 3 times with the following buffer solution: 20 mM Tris-HCl (pH=7.5), 200 mM LiCl and 1 mM EDTA. This has the effect of ensuring that the $NH_2$-dTTP-NitroB-Biot nucleotides introduced in excess are removed, leaving the reaction chamber and the solid support free of any unreacted nucleotide. At the end of the washing, 50 µl of a 20 mM Tris-HCl buffer (pH=7.5) are added to the reaction chamber and the temperature is increased to 90° C. This has the effect of ensuring the detachment of the fragments having incorporated the modified nucleotide $NH_2$-dTTP-NitroB-Biot. These fragments are collected and transferred into a new Eppendorf tube.

The DNA fragments having incorporated the protected nucleotide $NH_2$-dTTP-NitroB-Biot are then purified according to the following procedure. Commercial magnetic beads coated with streptavidin (ThermoScientific) prepared according to the manufacturer's protocol are added to the 50 µl of the previous reaction mixture. After incubation for 1 h at ambient temperature, the magnetic beads are collected by means of a suitable magnet. The supernatant is then removed. The beads are then washed 3 times with the washing buffer: tris buffer, pH 7.2, with 0.1% of Tween-20.

The magnetic beads to which the DNA fragments having incorporated the modified nucleotides $NH_2$-dTTP-NitroB-Biot are attached are resuspended in a solution comprising 350 to 700 mM of $NaNO_2$ and 1M NaOAc at pH 5.5. The mixture is incubated for 1 to 2 min at ambient temperature under exposure to UV (365 nm). The reaction is stopped by adding 1M phosphate buffer at pH 7.0 and stopping the illumination. This operation enables the "detachment" of the DNA fragments from their supports (beads).

The magnetic beads are collected by means of a suitable magnet. The supernatant is recovered and analyzed by electrophoresis gel and MALDI-TOF MS spectrometer in order to verify the correct incorporation of the T base at the 3' end of the sequence No. 1 in more than 99% of cases.

A new elongation step may then be carried out if necessary, according to the same protocol.

Example 13—Other Example of Use of Nucleotides According to the Invention for a Nucleic Acid Synthesis The modified nucleotides which are the subject of the present invention can be advantageously used to carry out the enzymatic synthesis of nucleic acids without the presence of template strands according to the process described in patent application FR 14-53455. The enzyme chosen for carrying out the step of adding the modified nucleotides is the commercially available terminal deoxynucleotidyl transferase or TdT.

The primer used to initiate the synthesis is given below:

```
5'-AGCCAAGCGGTCGCGATGAT-3'     Seq No 1
```

The modified nucleotides used are $NH_2$-dGTP-NitroB-Biot prepared according to Example 2. They make it possible to add a G to the sequence No. 1 presented. It is expected that only one nucleotide will be added to each DNA fragment during each elongation step, as described below.

A glass plate exhibiting capture fragments having the following sequence:

```
                                Seq No 2
5'-GTCCGCTTGGCT-3'
``` and attached to this glass plate by their 3' end, is used to capture the primers of sequence 1. This glass plate constitutes the base of a parallelepipedal reaction chamber having a volume of 50 µl. The capture is carried out using a buffer solution comprising: 20 mM Tris-HCl (pH=7.5), 500 mM LiCl and 1 mM EDTA to which are added 2 pmol of primer. The capture step is carried out over the course of 30 min at ambient temperature. Once the primers have been captured, the plate is washed by adding and removing 3 times 50 µl of the following buffer solution: 20 mM Tris-HCl (pH=7.5), 200 mM LiCl and 1 mM EDTA.

The synthesis begins with the addition of the following reagents to the reaction chamber: 50 U of TdT, 1M of potassium cacodylate, 125 mM of Tris-HCl, 0.05% (v/v) of Triton X-100, 5 mM of $CoCl_2$, pH 7.2. Next are added 100 µM of nucleotides $NH_2$-dGTP-NitroB-Biot which are free and in solution with their counterions. The enzyme at 2 µM is finally added in order to start the addition reaction. The total reaction volume is 50 µl. The mixture is incubated for 5 min at 37° C.

Once the synthesis reaction is complete, the plate is washed 3 times with the following buffer solution: 20 mM Tris-HCl (pH=7.5), 200 mM LiCl and 1 mM EDTA. This has the effect of ensuring that the $NH_2$-dGTP-NitroB-Biot nucleotides introduced in excess are removed, leaving the reaction chamber and the solid support free of any unreacted nucleotide. At the end of the washing, 50 µl of a 20 mM Tris-HCl buffer (pH=7.5) are added to the reaction chamber and the temperature is increased to 90° C. This has the effect of ensuring the detachment of the fragments having incorporated the modified nucleotide $NH_2$-dGTP-NitroB-Biot. These fragments are collected and transferred into a new Eppendorf tube.

The DNA fragments having incorporated the protected nucleotide $NH_2$-dGTP-NitroB-Biot are then purified according to the following procedure. Commercial magnetic beads coated with streptavidin (ThermoScientific) prepared according to the manufacturer's protocol are added to the 50 µl of the previous reaction mixture. After incubation for 1 h at ambient temperature, the magnetic beads are collected by means of a suitable magnet. The supernatant is then removed. The beads are then washed 3 times with the washing buffer solution: tris buffer, pH 7.2, with 0.1% of Tween 20.

The magnetic beads to which the DNA fragments having incorporated the modified nucleotides $NH_2$-dGTP-NitroB-Biot are attached are resuspended in a solution comprising 350 to 700 mM of $NaNO_2$ and 1M NaOAc at pH 5.5. The mixture is incubated for 1 to 2 min at ambient temperature with exposure to UV (365 nm). The reaction is stopped by adding 1M phosphate buffer, pH 7.0, and stopping the illumination. This operation allows the "detachment" of the DNA fragments from their supports (beads).

The magnetic beads are collected by means of a suitable magnet. The supernatant is recovered and analyzed by electrophoresis gel and MALDI-TOF MS spectrometer in order to verify the correct incorporation of the T base at the 3' end of the sequence No. 1 in more than 99% of cases.

If necessary, a new elongation step can then be carried out according to the same protocol.

INDUSTRIAL APPLICATION

The modified nucleotides which are subjects of the present invention improve the performance levels of nucleic acid synthesis processes by allowing in particular the synthesis of very long nucleic acids of very high quality. These nucleotides can be used for the production, on a more or less large scale, of synthetic nucleic acid sequences or genes. These modified nucleotides are particularly intended for the synthesis of nucleic acids such as DNA or RNA for research, development or industrialization purposes in the biotechnology field or more generally in the broad field of biology.

The invention claimed is:

1. A modified nucleotide comprising:

a "natural" nitrogenous base or a natural nitrogenous base analog, a ribose or deoxyribose carbohydrate, and at least one phosphate group, at least one R or R' group, called modifier group, borne:

by said natural nitrogenous base or analog, and/or by the oxygen in position 3' of the ribose or deoxyribose molecule, making it possible to block the polymerization of said nucleotide and/or to allow the interaction of said nucleotide with another molecule, different than another nucleotide, such as a protein, during nucleic acid synthesis, R comprising at least one functional end group, said nucleotide being in the form of one of formulae (I), (III) and (IV) below:

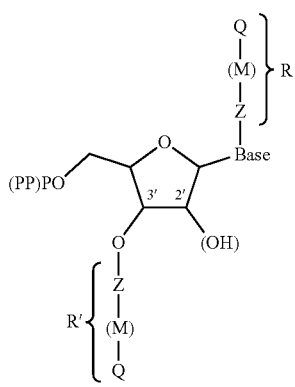
(Formula I)

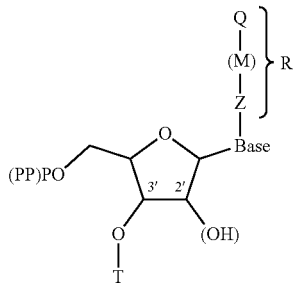
(Formula III)

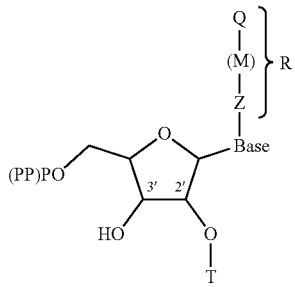
(Formula IV)

in which:

(PP)PO represents a mono-, di- or triphosphate group, (OH) describes the possibility of a ribose or deoxyribose molecule, T is a hydrogen, or a cleavable radical chosen from $-NH_2$, $-N_3$, $-(C=O)H$, $-C_nH_{2n+1}$ with n between 1 and 30, preferably between 1 and 12, -trimethylsilyl, -phosphate, $-SO3$, $-(C=O)OC_nH_{2n+1}$ with n between 1 and 30, preferably between 1 and 12, $-(C=O)SC_nH_{2n+1}$ with n between 1 and 30, preferably between 1 and 12, -nitrobenzene, -benzyl, -halobenzyl, -amide, -carbonate, -benzoyl, -peroxyl, -nitrile, -thiol, -imide, -carbamate, -cyanate, -alkyne, -phenyl, -halophenyl, -picolyl, M, which is optionally present, is a group covalently bonded to Q and to Z, M being chosen from alkyl, alkenyl, alkyne, aryl, alkylaryl, heteroaryl, acyl, alkyloxy, alkylamino, alkoxyamino, amido, alkylimido, alkenylimido, arylimido, fluoroalkyl, alkylphosphate, alkylthio, thioacyl, alkylsulfonyl, arylsulfonyl, alkylsulfinyl, alkylammonium, alkylsulfonium, alkylsilyl, alkylcarbonyl, alkylcarbanyl, alkylcarbamoyl or alkylhydroxylamino, Z is a cleavable -nitrophenyl-group, Q is an end functional, or effector, group of the R or R' group, Q being chosen from biotin, a protein, a polynucleotide of defined sequence, a carbohydrate, an antigen, a hormone, a neurotransmitter, a glycoside such as digoxin, a sulfur-containing radical, in particular bearing a thiol function, such as glutathione, or a bidentate ligand such as catechol, R and R' possibly being present independently or simultaneously, and when R and R' are present simultaneously:

the Z groups may be identical or different, the M groups may be identical or different, the Q groups may be identical or different, "base" represents a "natural" nitrogenous base chosen from adenine, thymine, cytosine, guanine or uracil or a natural nitrogenous base analog, with the exception of thymine when R' is present and Q comprises biotin.

2. The nucleotide as claimed in claim 1, wherein the modifier group R is borne by the nitrogenous base and forms one of the structures (V) below:

Adenine-based structure ($V_a$)

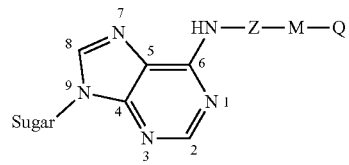

Thymine-based structure ($V_t$)

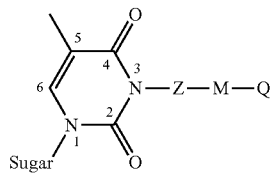

Cytosine-based structure ($V_c$)

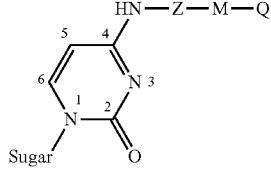

Guanine-based structure ($V_g$)

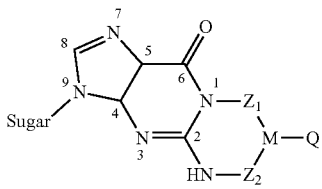

Uracil-based structure ($V_u$)

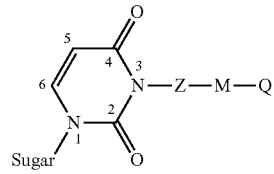

in which structures:

"sugar" represents the bond between said nitrogenous base and the ribose or deoxyribose molecule of the nucleotide molecule, $Z_1$ and $Z_2$ are identical or different, cleavable Z groups.

3. The nucleotide as claimed in claim 2, wherein the modifier group R borne by the nitrogenous base forms one of the structures (VI) below:

Adenine-based structure ($VI_a$)

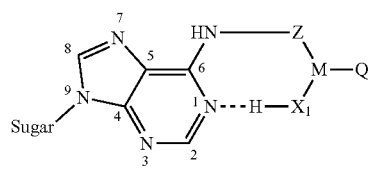

Thymine-based structure ($VI_t$)

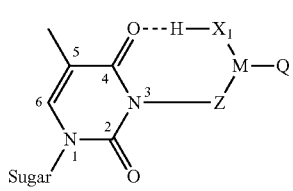

Cytosine-based structure ($VI_c$)

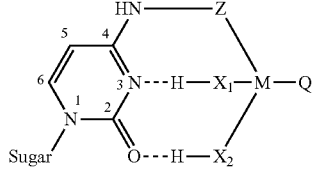

Guanine-based structure ($VI_g$)

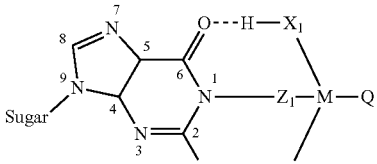

Uracil-based structure ($VI_u$)

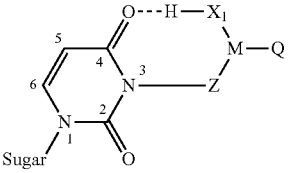

in which:

"Sugar" represents the bond between the nitrogenous base and the ribose or deoxyribose molecule of the nucleotide molecule, $X_1$ and $X_2$, which may be identical or different, represent nitrogen, oxygen or sulfur atoms borne by M and capable of forming, with said nitrogenous bases of the modified nucleotide, intermolecular hydrogen bonds (similar to those observed during conventional pairings between complementary nucleotides).

4. The nucleotide as claimed in claim 1, which can be used as a substrate for polymerases that are normally dependent on the presence of a template nucleic acid strand complementary to the strand undergoing synthesis, even in the absence of a complementary strand.

5. The nucleotide as claimed in claim 1, wherein the functional end radical Q of the R or R' group is capable of interacting with molecules other than a nucleic acid according to one or another of the following interaction pairs: antigen/antibody, hormone/receptor, biotin/(strept)avidin, neurotransmitter/receptor, polymerase/promoter, digoxin/antidigoxin, carbohydrate/lectin, sulfur-containing radical/metal such as gold, glutathione/glutathione S-transferase, bidentate ligand/metal oxide.

6. The nucleotide as claimed in claim 3, for which $X_1$ and $X_2$ are —NH, T is —$NH_2$, Z is —$CH_2$, M is methylnitrobenzyl-, and Q is -biotin.

7. The nucleotide as claimed in claim 3, for which $X_1$ and $X_2$ are —NH, T is —$NH_2$, Z, $Z_1$ and $Z_2$ are each —O—, M is -nitronaphthyl- and Q is -biotin.

8. The nucleotide of formula (I) as claimed in claim 1, bearing only the R' group in which: Z is —(C=O)—, M is —$C_8H_{16}$— and Q is —NH— biotinyl.

9. The nucleotide as claimed in claim 2, wherein the particular structure (V) in which Z, $Z_1$ and $Z_2$ are each —(COO)—, M is -tert-butylnitrobenzyl- and Q is —NH— biotinyl.

10. The nucleotide as claimed in claim 1, wherein T and Z, or $Z_1$, $Z_2$ are cleavable, during the nucleic acid synthesis, by irradiation of said nucleotide by means of electromagnetic radiation having a wavelength of between $10^{-3}$ and $10^{-11}$ meter, in particular by ultraviolet radiation.

11. A kit for nucleic acid synthesis, comprising at least one modified nucleotide as claimed in claim 1.

12. The kit as claimed in claim 11, for incorporating said nucleotide into a polynucleotide chain previously immobilized on a solid support, comprising various modified nucleotides, an elongation enzyme and a solid support capable of attaching at least one of said nucleotides.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: artificial sequence
<220> FEATURE:
<223> OTHER INFORMATION: synthetic sequence

<400> SEQUENCE: 1
agccaagcgg tcgcgatgat                                             20

<210> SEQ ID NO 2
<211> LENGTH: 12
<212> TYPE: DNA
<213> ORGANISM: artificial sequence
<220> FEATURE:
<223> OTHER INFORMATION: synthetic sequence

<400> SEQUENCE: 2
gtccgcttgg ct                                                     12
```